(12) United States Patent
Nirenberg

(10) Patent No.: US 11,430,263 B2
(45) Date of Patent: Aug. 30, 2022

(54) MACHINE VISION WITH DIMENSIONAL DATA REDUCTION

(71) Applicant: Cornell University, Ithaca, NY (US)

(72) Inventor: Sheila Nirenberg, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 111 days.

(21) Appl. No.: 16/724,145

(22) Filed: Dec. 20, 2019

(65) Prior Publication Data
US 2020/0143138 A1    May 7, 2020

Related U.S. Application Data

(63) Continuation of application No. 15/567,407, filed as application No. PCT/US2016/028406 on Apr. 20, 2016, now Pat. No. 10,515,269.
(Continued)

(51) Int. Cl.
*G06K 9/00* (2022.01)
*G06V 40/18* (2022.01)
(Continued)

(52) U.S. Cl.
CPC .............. *G06V 40/193* (2022.01); *A61F 9/08* (2013.01); *G06K 9/6256* (2013.01); *G06N 3/008* (2013.01);
(Continued)

(58) Field of Classification Search
None
See application file for complete search history.

(56) References Cited

U.S. PATENT DOCUMENTS 5,103,306 A    4/1992   Weiman et al.
5,717,834 A    2/1998   Werblin et al.
(Continued)

FOREIGN PATENT DOCUMENTS

CN    1770177 A    5/2006
CN    1985514 A    6/2007
(Continued)

OTHER PUBLICATIONS

Ahuja, A.K. et al., "Blind subjects implanted with the Argus II retinal prosthesis are able to improve performance in a spatial-motor task," Br J Ophthalmol, (2011), vol. 95, pp. 539-543.
(Continued)

*Primary Examiner* — Leon Viet Q Nguyen
(74) *Attorney, Agent, or Firm* — Foley & Lardner LLP

(57) ABSTRACT

A method is described that includes receiving raw image data corresponding to a series of raw images, and processing the raw image data with an encoder of a processing device to generate encoded data. The encoder is characterized by an input/output transformation that substantially mimics the input/output transformation of at least one retinal cell of a vertebrate retina. The method also includes processing the encoded data to generate dimension reduced encoded data by applying a dimension reduction algorithm to the encoded data. The dimension reduction algorithm is configured to compress an amount of information contained in the encoded data. An apparatus and system usable with such a method is also described.

19 Claims, 12 Drawing Sheets

Related U.S. Application Data

(60) Provisional application No. 62/150,068, filed on Apr. 20, 2015.

(51) Int. Cl.

| | | |
|---|---|---|
| *G06N 3/04* | (2006.01) | |
| *A61F 9/08* | (2006.01) | |
| *H04N 19/60* | (2014.01) | |
| *H04N 19/85* | (2014.01) | |
| *G06N 3/00* | (2006.01) | |
| *G06V 10/20* | (2022.01) | |
| *G06V 10/44* | (2022.01) | |
| *G06V 40/19* | (2022.01) | |
| *G06V 40/10* | (2022.01) | |
| *G06K 9/62* | (2022.01) | |
| *G06N 3/08* | (2006.01) | |

(52) U.S. Cl.
CPC ........... *G06N 3/049* (2013.01); *G06N 3/0454* (2013.01); *G06N 3/08* (2013.01); *G06V 10/20* (2022.01); *G06V 10/449* (2022.01); *G06V 10/454* (2022.01); *G06V 40/103* (2022.01); *G06V 40/19* (2022.01); *H04N 19/60* (2014.11); *H04N 19/85* (2014.11)

(56) References Cited

U.S. PATENT DOCUMENTS

| | | |
|---|---|---|
| 5,815,608 A | 9/1998 | Lange et al. |
| 5,836,996 A | 11/1998 | Doorish |
| 5,856,152 A | 1/1999 | Wilson et al. |
| 5,871,982 A | 2/1999 | Wilson et al. |
| 5,974,159 A | 10/1999 | Lubin et al. |
| 6,400,989 B1 | 6/2002 | Eckmiller |
| 6,458,157 B1 | 10/2002 | Suaning |
| 6,530,954 B1 | 3/2003 | Eckmiller |
| 6,533,798 B2 | 3/2003 | Greenberg et al. |
| 6,801,655 B2 | 10/2004 | Woodall |
| 7,149,586 B2 | 12/2006 | Greenberg et al. |
| 8,103,352 B2 | 1/2012 | Fried et al. |
| 8,108,147 B1 | 1/2012 | Blackburn |
| 8,467,623 B2 | 6/2013 | Izhikevich et al. |
| 8,956,396 B1 | 2/2015 | Friend et al. |
| 9,302,103 B1 | 4/2016 | Nirenberg |
| 9,547,804 B2 | 1/2017 | Nirenberg et al. |
| 2002/0111655 A1 | 8/2002 | Scribner |
| 2002/0161417 A1 | 10/2002 | Scribner |
| 2002/0168100 A1 | 11/2002 | Woodall |
| 2002/0194159 A1 | 12/2002 | Kamath et al. |
| 2003/0088081 A1 | 5/2003 | Maliga et al. |
| 2003/0093129 A1 | 5/2003 | Nicolelis et al. |
| 2003/0105409 A1 | 6/2003 | Donoghue et al. |
| 2003/0235341 A1 | 12/2003 | Gokturk et al. |
| 2004/0147975 A1 | 7/2004 | Popovic et al. |
| 2004/0176821 A1 | 9/2004 | Delbeke et al. |
| 2005/0015120 A1 | 1/2005 | Seibel et al. |
| 2006/0005160 A1 | 1/2006 | Schultz et al. |
| 2006/0129207 A1 | 6/2006 | Fried et al. |
| 2006/0184062 A1 | 8/2006 | Greenberg et al. |
| 2006/0251621 A1 | 11/2006 | Campochiaro et al. |
| 2007/0050046 A1 | 3/2007 | Georgopoulos |
| 2007/0198066 A1 | 8/2007 | Greenberg et al. |
| 2007/0261127 A1 | 11/2007 | Boyden et al. |
| 2008/0021515 A1 | 1/2008 | Horsager et al. |
| 2008/0021516 A1 | 1/2008 | Greenberg et al. |
| 2008/0086206 A1 | 4/2008 | Nasiatka et al. |
| 2008/0095450 A1 | 4/2008 | Kirenko |
| 2008/0221653 A1 | 9/2008 | Agrawal et al. |
| 2008/0234781 A1 | 9/2008 | Einav et al. |
| 2008/0249588 A1 | 10/2008 | Greenberg et al. |
| 2008/0294217 A1 | 11/2008 | Lian et al. |
| 2009/0088399 A1 | 4/2009 | Balya et al. |
| 2009/0105786 A1 | 4/2009 | Fetz et al. |
| 2009/0118793 A1 | 5/2009 | Mcclure et al. |
| 2009/0118794 A1 | 5/2009 | Mcclure et al. |
| 2009/0326623 A1 | 12/2009 | Greenberg et al. |
| 2010/0008568 A1 | 1/2010 | Curti et al. |
| 2010/0015095 A1 | 1/2010 | Pan et al. |
| 2010/0016732 A1 | 1/2010 | Wells et al. |
| 2010/0036457 A1 | 2/2010 | Sarpeshkar et al. |
| 2010/0135591 A1 | 6/2010 | Zador |
| 2010/0147961 A1 | 6/2010 | Gavin |
| 2010/0152849 A1 | 6/2010 | Degenaar et al. |
| 2010/0165117 A1* | 7/2010 | Kim ..................... G06T 1/00 348/207.1 |
| 2010/0183217 A1 | 7/2010 | Seung et al. |
| 2010/0234273 A1 | 9/2010 | Boyden et al. |
| 2010/0262212 A1 | 10/2010 | Shoham et al. |
| 2010/0272688 A1 | 10/2010 | Acland et al. |
| 2010/0286748 A1 | 11/2010 | Midani et al. |
| 2001/0911102 | 4/2011 | Cimbalista |
| 2011/0091102 A1 | 4/2011 | Cimbalista, Jr. |
| 2011/0213266 A1 | 9/2011 | Williams et al. |
| 2011/0270352 A1 | 11/2011 | Nanduri et al. |
| 2011/0307079 A1 | 12/2011 | Oweiss et al. |
| 2012/0123293 A1 | 5/2012 | Shah et al. |
| 2012/0303091 A1 | 11/2012 | Izhikevich |
| 2013/0110236 A1 | 5/2013 | Nirenberg |
| 2013/0289668 A1 | 10/2013 | Nirenberg et al. |
| 2014/0034796 A1 | 2/2014 | Hering et al. |
| 2014/0355861 A1 | 12/2014 | Nirenberg et al. |
| 2014/0364796 A1 | 12/2014 | Fridman et al. |
| 2016/0104031 A1 | 4/2016 | Shotton et al. |

FOREIGN PATENT DOCUMENTS

| | | |
|---|---|---|
| CN | 101017535 A | 8/2007 |
| CN | 101239008 A | 8/2008 |
| CN | 101336856 A | 1/2009 |
| CN | 101393789 A | 3/2009 |
| CN | 103890781 A | 6/2014 |
| EP | 1 864 690 A2 | 12/2007 |
| EP | 1 891 976 A1 | 2/2008 |
| JP | 06-139361 | 5/1994 |
| JP | 2002-503360 A | 1/2002 |
| JP | 2007-293559 A | 11/2007 |
| JP | 2009-540900 A | 11/2009 |
| JP | 2014-524630 A | 9/2014 |
| KR | 10-2004-0064930 | 7/2004 |
| WO | WO-96/13598 | 5/1996 |
| WO | WO-98/48027 | 10/1998 |
| WO | WO-00/15822 | 3/2000 |
| WO | WO-01/94605 A2 | 12/2001 |
| WO | WO-03/047525 A2 | 6/2003 |
| WO | WO-03/080648 A2 | 10/2003 |
| WO | WO-03/093479 A1 | 11/2003 |
| WO | WO-03/104413 A2 | 12/2003 |
| WO | WO-2005/080573 A1 | 9/2005 |
| WO | WO-2007/127428 A2 | 11/2007 |
| WO | WO-2009/126112 | 10/2009 |
| WO | WO-2010/011404 A2 | 1/2010 |
| WO | WO-02/082904 A2 | 10/2012 |
| WO | WO/2013/029008 * | 2/2013 ............... G06K 9/20 |
| WO | WO 2013/029008 A1 | 2/2013 |
| WO | WO-2013/029008 A1 | 2/2013 |

OTHER PUBLICATIONS

Arenkiel, Benjamin R. et al., "In vivo light-induced activation of neural circuitry in transgenic mice expressing channelrhodopsin-2," Neuron, (Apr. 19, 2007), vol. 54(2), pp. 205-218.

Asher, et al. "Image Processing for a High-Resolution Optoelectronic Retinal Prosthesis", IEEE Transactions On Biomedical Engineering, Jun. 1, 2007, vol. 54, No. 6 pp. 993-1004.

Ausubel et al., Current Protocols In Molecular Biology, "Overview of the HIV-1 Lentivivral Vector System", John Wiley & Sons, New York, (1989), Unit 16.21, 15 pgs.

Ausubel et al., Current Protocols In Molecular Biology, "Production of Recombinant Adeno-Associated Viral Vectors for In Vitro and In

(56) References Cited

OTHER PUBLICATIONS

Vivo Use", John Wiley & Sons, New York, (1989), Unit 16.25, 24 pgs.
Ausubel, Frederick M. et al., "Current Protocols in Molecular Biology," (2003), John Wiley & Sons, New York, Chapter 1 Only, 7 pages.
Averback et al., Effects of Noise Correlations on Information Encoding and Decoding, J Neurophysiol, vol. 95, 2006, pp. 3633-3644.
Bach, M. et al., "Visual evoked potential-based acuity assessment in normal vision, artificially degraded vision, and in patients," Br J Ophthalmol, (2008), vol. 92, pp. 396-403.
Ballard et al., Computer Vision, Prentice-Hall Inc New Jersey, 1982, (Table of Contents).
Barnstable, C.J. et al., "Thy-1 antigen: a ganglion cell specific marker in rodent retina," Neuroscience, (1984), vol. 11, No. 4, pp. 847-855.
Barranaca et al., "Sparsity and Compressed Coding in Sensory Systems," PLOS Computational Biology, Aug. 21, 2014, 32 pages.
Bl, Anding et al., "Ectopic expression of a microbial-type rhodopsin restores visual responses in mice with photoreceptor degeneration," Neuron, (Apr. 6, 2006), vol. 50, pp. 23-33.
Bomash I. et al., "A virtual retina that works on a broad array of stimuli including natural scenes: A tool to simplify the problem of population coding," 40th Annual Neuroscience Presentation, Society for Neuroscience (2010) Program No. 891.5, 2 pages.
Bookstein, Robert et al., "Promoter deletion and loss of retinoblastoma gene expression in human prostate carcinoma," Proc. Natl. Acad. Sci. USA, (Oct. 1990), vol. 87, pp. 7762-7766.
Brown CJ et al., The Relationship Between EAP and EABR Thresholds and Levels Used to PRogram the Nucleus 24 Speech Processor: Data from Adults, Ear and Hearing, vol. 21, No. 2, 2000, pp. 151-163.
Busskamp, Volker et al., "Genetic reactivation of cone photoreceptors restores visual responses in retinitis pigmentosa," Science, (Jul. 2010), vol. 329, pp. 413-417.
Cai, Xue et al., "Gene delivery to mitotic and postmitotic photoreceptors via compacted DNA nanoparticles results in improved phenotype in a mouse model of retinitis pigmentosa," FASEB J., (Apr. 2010), vol. 24, pp. 1178-1191.
Campagnola, Luke et al., "Fiber-coupled light-emitting diode for localized photostimulation of neurons expressing channelrhodopsin-2," Journal of Neuroscience Methods, (2008), vol. 169, pp. 27-33.
Canadian Office Action, App. No. 2,883,091 (dated Jul. 16, 2018).
Cardin, Jesicca A. et al., "Targeted optogenetic stimulation and recording of neurons in vivo using cell-type-specific expression of Channelrhodopsin-2," Nat Protoc, (2010), vol. 5, No. 2, pp. 247-254.
Cescon C. et al., "Non-invasive characterization of single motor unit electromyographic and mechanomyographic activities in the biceps brachii muscle", J Electromyogr Kinesiol, vol. 16, No. 1, Epub Aug. 19, 2005, pp. 17-24.
Chader, Gerald J. et al., "Artificial vision: needs, functioning, and testing of a retinal electronic prosthesis," Prog Brain Res, (2009), vol. 175, pp. 317-332.
Chen, Xiaowei et al., "HSV amplicon-mediated neurotrophin-3 expression protects murine spiral ganglion neurons from cisplatin-induced damage", Mol Ther., (Jun. 2001), vol. 3, No. 6, pp. 958-963.
Chestek, Cynthia A. et al., "HermesC: Low-Power Wireless Neural Recording System for Freely Moving Primates" IEEE, (Aug. 2009), vol. 17, No. 4, pp. 268-275.
Chiappa, K., "Principals of Evoked Potentials," Evoked Responses in Clinical Medicine, Third Edition, Lippincott-Raven Publishers, (1997), pp. 1-30.
Chichilnisky, E.J., "A simple white noise analysis of neuronal light responses," Network: Comput. Neural Syst., (2001), vol. 12, pp. 199-213.
Chopdar, Amresh et al., "Age related macular degeneration," BMJ, (Mar. 2003), vol. 326, pp. 485-488.

Communication pursuant to Article 94(3) EPC EP 12825425.7 dated Dec. 11, 2019 (4 pages).
Communication pursuant to Rules 161(2) and 162 EPC in EP Appln No. 118223282.5 dated Apr. 12, 2013.
Cover, Thomas M. et al., "Elements Of Information Theory," 2nd Edition, John Wiley & Sons, Inc., Hoboken, NJ, Wiley (2006), 4 pages.
Dann, Joan F. et al., "Retinal ganglion cells projecting to the accessory optic system in the rat," J Comp Neurol, (1987), vol. 262, pp. 141-158.
Dedek, Karin et al., "Ganglion cell adaptability: does the coupling of horizontal cells play a role?" PLoS One, (Mar. 2008), vol. 3, Issue 3, pp. e1714, 10 pages.
Douglas et al., "Independent Visual Threshold Measurements In The Two Eyes Of Freely Moving Rats And Mice Using A Virtual-Reality Optokinetic System," Visual Neuroscience, 22(5):677-684 (2005).
Duda, R.O. et al., "Multilayer Neural Networks," Pattern Classification (2nd Edition) Chapter 6, Wiley, NY (2001), 78 pages.
Eckmiller et al., "Tunable Retina Encoders for Retina Implants: Why and How," Journal or Nueral Engineering, (2005) 2(1), pp. S91-S104.
Eckmiller, R. et al., "Dialog Concepts for Learning Retina Encoders," IEEE International Conference on Neural Networks Proceedings, (Jun. 1, 1997), vol. 4, pp. 2315-2320.
Enroth-Cugell et al., "The Contrast Sensitivity Of Retinal Ganglion Cells Of The Cat," The Journal Of Physiology, 187(3):517-552 (1966).
Exam Report issued on European Application 15201184.7, dated Feb. 12, 2018.
Examination Report received in European Patent Application 11748237.2 dated Sep. 3, 2014, 5 pages.
Examination Report received in European Patent Application No. 11748237.2 dated Apr. 16, 2014, 6 pages.
Examination Report received in European Patent Application No. 11822382.5 dated Oct. 27, 2014, 6 pages.
Extended European Search Report and Search Opinion for European Application No. 11748237.2, dated Jul. 19, 2013.
Extended European Search Report, App. No. 16783749.1 (dated Jan. 3, 2019).
Extended Search Report received for European Patent Application No. 12825425.7 dated May 23, 2016, 10 pages.
Extended Search Report received in European Patent Application No. 11822382 dated Feb. 14, 2014, 8 pages.
Famulare M, Fairhall A., "Feature Selection In Simple Neurons: How Coding Depends On Spiking Dynamics," Neural Computation 22(3):581-598 (2010).
Field, G.D. et al., "Information processing in the primate retina: circuitry and coding," Annu Rev Neurosci, (2007), vol. 30, pp. 1-30.
Final Office Action issued in U.S. Appl. No. 15/073,002 dated Aug. 9, 2016, 27 pages.
Final Office Action on U.S. Appl. No. 15/408,178 dated Mar. 7, 2018.
Final Office Action on U.S. Appl. No. 15/567,407 dated Jun. 26, 2019.
Final Office Action received for U.S. Appl. No. 14/239,828 dated Apr. 15, 2016, 28 pages.
Final Office Action received in U.S. Appl. No. 13/230,488 dated Nov. 26, 2014, 24 pages.
First Examination Report received in Australian Patent Application No. 2011220367 dated Jul. 13, 2015, 5 pages.
First Office Action from Chinese Application No. 201180021117.2 dated May 6, 2014, 15 pages—with English Translation.
First Office Action received in Chinese Patent Application No. 201180051504.0 dated Oct. 10, 2014, first received Nov. 25, 2014, 16 pages with English translation.
Fitzgerald, Kathleen M. et al., "Retinal Signal Transmission in Duchenne Muscular Dystrophy: Evidence for Dysfunction in the Photoreceptor/Depolarizing Bipolar Cell Pathway," J Clin Invest, (Jun. 1994), vol. 93, pp. 2425-2430.
Foley, John M. et al., "Contrast Detection and Near-Threshold Discrimination in Human Vision," Vision Res., (1981), vol. 21, pp. 1041-1053.

(56) References Cited

OTHER PUBLICATIONS

Foreign Action other than Search Report on CN 201680032611.1 dated Jul. 26, 2019.
Foreign Action other than Search Report on KR 10-2019-7012590 dated Aug. 5, 2019.
Foreign Action other than Search Report on non-Foley case related to CA 2883091 dated Jun. 20, 2019.
Forsyth, D.A. et al., Computer Vision: A Modern Approach, Second edition, Prentice Hall, (2011).
Franck KH., "A model of a nucleus 24 cochlear implant fitting protocol based on the electrically evoked whole nerve action potential", Ear & Hearing, vol. 23, No. 18, 2002, pp. 67S-71S.
Freund, Y. et al., "A Decision-Theoretic Generalization of on-Line Learning and an Application to Boosting," Journal of Computer and System Sciences (1997) 55, 119-139.
Friedman DS, et al., "Prevalence Of Age-Related Macular Degeneration In The United States," Epidemiology, Eye Diseases Prevalence Research Group, Archives Of Ophthalmology 122 (4):564-572 (Apr. 2004).
Friedman, David S. et al., Eye Diseases Prevalence Research Group, "Prevalence of age-related macular degeneration in the United States," Arch Ophthalmol, (Apr. 2004), vol. 122, No. 4, pp. 564-572.
Geisler, Wilson S., "Visual perception and the statistical properties of natural scenes" Annu. Rev. Psychol., (2008), vol. 59, pp. 167-192.
Gerding, H. et al., "Experimental implantation of epiretinal retina implants (EPI-RET) with an IOL-type receiver unit," J Neural Eng, (2007), vol. 4, pp. S38-S49.
Giolli, Roland A. et al., "The accessory optic system: basic organization with an update on connectivity, neurochemistry, and function," Prog Brain Res, (2005), vol. 151, pp. 407-440.
Golan, L. et al., "Design and characteristics of holographic neural photo-stimulation systems," Journal of Neural Engineering, (2009), vol. 6, 14 pages.
Gollisch et al., Rapid Neural Coding in the Retina with Relative Spike Latencies.: In:Science, Feb. 22, 2008, 11 pages.
Graham-Rowe, Duncan, "A Brighter Future for Retinal Implants: Implants may be common place in only a couple of years," MIT Technology Review, http://www.technologyreview.com/biomedicine/23539/. Boston, MA: MIT (2009), 2 pages.
Greenberg, Kenneth P. et al., "Differential Targeting of Optical Neuromodulators to Ganglion Cell Soma and Dendrites Allows Dynamic Control of Center-Surround Antagonism," Neuron, (Feb. 2011), vol. 69, pp. 713-720.
Grinstead, Charles M. et al., "Introduction To Probability," American Mathematical Society, 2nd Revised Edition, Chapter 1 only,(1997), 7 pages.
Grossman, Nir et al., "Multi-site optical excitation using ChR2 and micro-LED array," J. Neural Eng., (2010), vol. 7, pp. 1-13.
Guiraud D. et al., "An implantable neuroprosthesis for standing and walking in paraplegia: 5-year patient follow-up", Journal of Neural Engineering, 2006, vol. 3, pp. 268-275.
Han, Xue et al., "Millisecond-Timescale Optical Control of Neural Dynamics in the Nonhuman Primate Brain," Neuron, Apr. 30, 2009, vol. 62, pp. 191-198.
Hand, "Discrimination And Classification," Wiley Series In Probability And Mathematical Statistics (1981).
Hochberg LR, et al., "Neuronal ensemble control of prosthetic devices by a human with tetraplegia", Nature, Jul. 13, 2006, vol. 442, pp. 164-171.
Huang et al., "An Optoelectronic Platform for Retinal Prosthesis," Biomedical Circuits and Systems Conference (BIOCAS 2006), IEEE, Nov. 29, 2006, pp. 110-113.
Huberman AD, et al., "Architecture And Activity-Mediated Refinement Of Axonal Projections From A Mosaic Of Genetically Identified Retinal Ganglion Cells," Neuron, 2008, 59(3), pp. 425-438.

Huberman AD, et al., "Genetic Identification Of An On-Off Direction-Selective Retinal Ganglion Cell Subtype Reveals A Layer-Specific Subcortical Map Of Posterior Motion," Neuron, 2009, 62(3), pp. 327-334.
International Preliminary Report on Patentability in PCT/US2011/049188 dated Mar. 14, 2013.
International Preliminary Report on Patentability issued on PCT/US2016/028406, dated Nov. 2, 2017.
International Search Report and Written Opinion from PCT/US2012/052348 dated Nov. 2, 2012, 9 pages.
International Search Report and Written Opinion issued on PCT/US2016/028406, dated Jul. 25, 2016.
International Search Report and Written Opinion of PCT/US2011/49188 dated Jan. 27, 2012.
International Search Report in PCT/US2011/026526 dated Apr. 22, 2011.
IPRP (Chapter I) from PCT/US2012/052348 dated Mar. 6, 2014, 7 pages.
Ivanova, E., Pan, Z-H, "Evaluation of the adeno-associated virus mediated long-term expression of channelrhodopsin-2 in the mouse retina." Molecular Vision, 2009, 15, pp. 1680-1689.
Izhikevich, "Hybrid Spiking Models," Review, Philosophical Transactions Of Royal Society A, 368:5061-5070 (2010).
Izhikevich, E.M., "Dynamical Systems in Neuroscience: The Geometry of Excitability and Bursting." Cambridge, MA: MIT Press (2007), 210 pages.
Jacobs et al., "Ruling Out And Ruling In Neural Codes," Proceedings Of The National Academy Of Sciences, vol. 106, No. 14: 5936-5941 (Apr. 7, 2009).
Jeffreys, Harold, The Theory of Probability. The Oxford University Press (1961).
Kass RE, et al., "Statistical Issues In The Analysis Of Neuronal Data," Journal Of Neurophysiology, 94(1):8-25 (2005).
Kawasaki et al., "Variability of the Relative Afferent Pupillary Defect," Am J Ophthalmol (1995) 120: 622-633.
Kay MA, et al., "Viral Vectors For Gene Therapy: The Art Of Turning Infectious Agents Into Vehicles Of Therapeutics," Nature Medicine, 7(1):33-40, Review (2001).
Kelly, S. et al., "Realization of a 15-Channel, Hermetically-Encased Wireless Subretinal Prosthesis for the Blind," 31st Annual International Conf of the IEEE EMBS, Minneapolis, MN (2009), pp. 200-203.
Kibbel, S. et al. "Design and Performance of an improved active subretinal chip." World Congress on Medical Physics and Biomedical Engineering, Sep. 7-12, 2009, Munich, Germany, IFMBE Proceedings vol. 25/8, 2010, pp. 192-195.
Kim RH et al., "Waterproof AlInGaP optoelectronics on stretchable substrates with applications in biomedicine and robotics", Nature Materials, 2010, vol. 9, pp. 929-937.
Koilkonda RD, et al., "Efficient Expression Of Self-Complementary AAV In Ganglion Cells Of The Ex Vivo Primate Retina," Molecular Vision, 15:2796-2802 (2009).
Korean Office Action, App. No. 10-2014-7007453 (dated Aug. 7, 2018).
Kuffler, S.W., "Discharge patterns and functional organization of mammalian retina," J Neurophysiol (1953) 16(1): 37-68.
Lagali PS, et al., "Light-Activated Channels Targeted To ON Bipolar Cells Restore Visual Function In Retinal Degeneration," Nature Neuroscience, 11 (6):667-675 (Jun. 2008).
Lee et al., "Variability and Correlated Noise in the Discharge of Neurons in Motor and Parietal Areas of the Primate Cortex", The Journal of Neuroscience, Feb. 1, 1998, vol. 18, No. 3, pp. 1161-1170.
Lei L. et al., "Efficient transduction of spiral ganglion cells using adenovirus type 5 vector in the rat", Acta Oto-Laryngologica, 2010, vol. 130, pp. 810-814.
Lesica et al., "Adaptation To Stimulus Contrast And Correlations During Natural Visual Stimulation," Neuron, 55(3):479-491 (Aug. 2, 2007).
Lettvin et al., "What The Frog's Eye Tells The Frog's Brain," Proceedings Of The Institute Of Radio Engineers 47(11): 1940-1951 (1959); Reprinted from: "The Mind: Biological Approaches to its Functions", Editors: William Corning, et al. 1968, pp. 233-258.

(56) References Cited

OTHER PUBLICATIONS

Liao et al., "In Vivo Gene Delivery In The Retina Using Polyethylenimine," Biotechniques, 42 (3):285-288 (2007).
Liu Y. et al., "Promoter effects of adeno-associated viral vector for transgene expression in the cochlea in vivo", Experimental and Molecular Medicine, Apr. 2007, vol. 38, No. 2, pp. 170-175.
Ljubo et al., "Intelligent Vehicle Technologies: Theory and Applications (Automotive Engineering Series)," pp. 85-170 (Jan. 6, 2002), retrieved from https://www.sciencedirect.com/book/9780750650939/intelligent-vehicle-technologies.
Loewenstein, J.I. et al., "Outer Retinal Degeneration: An Electronic Retinal Prosthesis as a Treatment Strategy," Arch Ophthalmol (2004) 122:587-596.
Luebke AE et al., "Adenoviral and AAV-mediated gene transfer to the inner ear: role of serotype, promoter, and viral load on in vivo and in vitro infection efficiencies", Adv. Otorhinolaryngol.Basel, Karger, 2009, vol. 66, pp. 87-98.
Maguire et al., "Safety And Efficacy Of Gene Transfer For Leber's Congenital Amaurosis," The New England Journal Of Medicine, 358 (21):2240-2248 (May 22, 2008).
Mancuso et al., "Gene Therapy For Red-Green Colour Blindness In Adult Primates," Nature, 461:784-787 (Oct. 8, 2009).
Martin et al., "Gene delivery to the eye using adeno-associated viral vectors." Methods (2002) 28:267-275.
McGowan, M.H. et al.,"Characterization of the Mouse Aldose Reductase Gene and Promoter in a Lens Epithelial Cell Line." Mol Vis (1998); 4:2, 8 pages.
Mclaughlin SK, et al., "Adeno-Associated Virus General Transduction Vectors: Analysis Of Proviral Structures," Journal Of Virology, 62(6):1963-1973 (1988).
Meytlis, et al. "Determining the role of correlated firing in large populations of neurons using white noise and natural scene stimuli", Vision Research, 2012, vol. 70, pp. 44-53.
Meytlis, M. et al., "Assessing the importance of correlated firing using large populations of neurons," Society for Neuroscience (2009) Program No. 165.3, 2 pages.
Morgans, C.W. et al., "TRPM1 is required for the depolarizing light response in retinal ON-bipolar cells," Proc Natl Acad Sci U.S.A. (2009) 106(45): 19174-8.
Moritz CT et al., "Direct control of paralysed muscles by cortical neurons", Nature, Dec. 2008, vol. 456, vol. 456, pp. 639-643.
Nanduri, D. et al., "Retinal prosthesis phosphene shape analysis," 30th Annual International Conference of the IEEE, Engineering in Medicine and Biology Society, Vancouver, BC, (2008) pp. 1785-1788.
New Zealand IPO First Examination Report dated Sep. 20, 2013 for New Zealand patent application 608804.
Nichols Z, Meytlis M, Nirenberg S., Correlations play a negligible role in coding white noise and natural scene stimuli in complete retinal populations. (2010), 3 pages, Submitted. Abstract only. http://physiology.med.cornell.edu/faculty/nirenberg/lab/marsha/papers.html.
Nirenberg et al., "Retinal Ganglion Cells Act Largely As Independent Encoders," Nature 411(6838):698-701 (Jun. 7, 2001).
Nirenberg, "Photoablation Of Cells Expressing Beta-Galactosidase," Methods In Molecular Biology, 135:475-480 (2000).
Nirenberg, S. and Cepko, C., Targeted Ablation of Diverse Cell Classes in the Nervous System in vivo. J Neurosci. (1993) 13(8):3238-3251.
Nirenberg, S. and Latham, P.E., "Population coding in the retina," Curr. Opin. Neurobiol. (1998) 8(4):488-493.
Nirenberg, S. and Meister, M., "The Light Response of Retinal Ganglion Cells is Truncated by a Displaced Amacrine Circuit," Neuron (1997) 18:637-650.
Nirenberg, S. et al., "Heterogeneous response dynamics in retinal ganglion cells: the interplay of predictive coding and adaptation," J Neurophysiol (2010) 103(6): 3184-94.
Nirenberg, S., "Photoablation of cells expressing beta-galactosidase," Methods Mol Biol. (2000) 135:475-80.

Non-Final Office Action in U.S. Appl. No. 13/230,488 dated Feb. 3, 2014.
Non-Final Office Action on U.S. Appl. No. 15/073,002 dated Mar. 1, 2017.
Non-Final Office Action on U.S. Appl. No. 15/408,178 dated Jul. 6, 2017.
Non-Final Office Action on U.S. Appl. No. 15/408,178 dated Jun. 27, 2018.
Non-Final Office Action on U.S. Appl. No. 15/567,407 dated Jan. 29, 2019.
Non-Final Office Action on U.S. Appl. No. 16/056,308 dated May 3, 2019.
Non-Final Office Action on U.S. Appl. No. 16/421,147 dated Dec. 10, 2019.
Non-Final Office Action received for U.S. Appl. No. 14/239,828 dated Sep. 9, 2015, 35 pages.
Non-Final Office Action received in U.S. Appl. No. 13/230,488 dated Jul. 2, 2015, 15 pages.
Non-Final Office Action received in U.S. Appl. No. 13/821,187 dated Jul. 30, 2014, 20 pages.
Norcia, A.M., et al., "Measurement of spatial contrast sensitivity with the swept contrast VEP," Vision Res. (1989), 29(5):627-637.
Norcia, AM et al. , "Spatial Frequency Sweep VEP: Visual Acuity During The First Year Of Life," Vision Research, 25(10):1399-1408 (1985).
Notice of Allowance on U.S. Appl. No. 14/239,828 dated Oct. 14, 2016.
Notice of Allowance on U.S. Appl. No. 14/981,242 dated Apr. 3, 2018.
Notice of Allowance on U.S. Appl. No. 15/073,002 dated Sep. 25, 2017.
Notice of Allowance on U.S. Appl. No. 15/073,002 dated Nov. 8, 2017.
Notice of Allowance on U.S. Appl. No. 15/408,178 dated Jan. 4, 2019.
Notice of Allowance on U.S. Appl. No. 15/567,407 dated Aug. 19, 2019.
Notice of Allowance on U.S. Appl. No. 15/567,407 dated Nov. 12, 2019.
Notice of Allowance on U.S. Appl. No. 16/056,308 dated Sep. 12, 2019.
Notice of Allowance received for U.S. Appl. No. 13/230,488 dated Nov. 24, 2015, 10 pages.
Notice of Allowance received for U.S. Appl. No. 13/595,812 dated Aug. 13, 2015, 37 pages.
Notice of Allowance received in U.S. Appl. No. 13/821,187 dated Jul. 8, 2015, 23 pages.
Novin et al., "Transforming of Images Information to the Implant Part of Retinal Prothesis, by Converting of Images to Bit Formats," Biomedical Engineering (ICBME), 2010 17th Iranian Conference of IEEE, pp. 1-4, Nov. 3, 2010.
Office Action issued for CN 201610124958.0 dated May 30, 2018.
Office Action issued on Chinese Application 201280052177.5, dated May 10, 2017, English translation only.
Office Action issued on Chinese Application 201610124958.0, dated Aug. 31, 2017.
Office Action issued on Chinese Application201280052177.5, dated Sep. 12, 2016, English translation only.
Office Action issued on Japanese Application 2015-238731, dated Nov. 21, 2016, English translation.
Office Action on EP Application 12825425.7, dated Mar. 15, 2019, 7 pages.
Office Action on U.S. Appl. No. 14/981,242 dated Oct. 10, 2017.
Office Action received for Japanese Patent Application No. 2014-527338 English translation only.
Office Action received in Japanese Patent Application No. 2012-555211 dated Nov. 5, 2014, 9 pages—with English translation.
Okuyama et al., "Binocular infrared optometer for measuring accommodation in both eyes simultaneously in natural-viewing conditions," Applied Optics, (1993) vol. 32. No. 22, pp. 4147-4154.
Pandarinath et al., "A novel mechanism for switching a neural system from one state to another," Front Comput Neurosci. 2010, 31(4): 2, pp. 1-18.

(56) References Cited

OTHER PUBLICATIONS

Pandarinath et al., "Symmetry Breakdown In The ON And OFF Pathways Of The Retina At Night: Functional Implications," Journal Of Neuroscience, 30(30):10006-10014 (Jul. 28, 2010).
Paninski, "Maximum Likelihood Estimation Of Cascade Point-Process Neural Encoding Models," Network: Comput. Neural Syst., 15(4):243-262 (2004).
Paninski, L. et al., "Statistical models for neural encoding, decoding, and optimal stimulus design," Prog Brain Res. (2007) 165:493-507.
Panzeri, S. et al., "Correcting for the Sampling Bias Problem in Spike Train Information Measures," J Neurophysiol. (2007) 98:1064-1072.
Pelli, D.G. et al., "The design of a new letter chart for measuring contrast sensitivity," Clinical Vision Sciences (1988) 2, 187-199.
Perry, V.H. and Silveira, L.C., "Functional lamination in the ganglion cell layer of the macaque's retina," Neuroscience (1988) 25(1):217-223.
Petersen-Jones et al., "AAV retinal transduction in a large animal model species: comparison of a self-complementary AAV2/5 with a single-stranded AAV2/5 vector," Mol Vis (2009) 15: 1835-1842.
Petrs-Silva et al., "High-efficiency transduction of the mouse retina by tyrosine-mutant AAV serotype vectors," Mol Therapy (2009) 17(3): 463-471.
Piedade et al., "Visual Neuroprothesis: A Non Invasive System for Stimulating the Cortex," IEEE Transactions on Circuits and Systems—I: Regular Papers, (Dec. 2005), vol. 53, No. 10, pp. 2648-2662.
Pillow, J.W. et al., "Spatio-temporal correlations and visual signalling in a complete neuronal population," Nature (2008) 454(7207): 995-999.
Prusky, G.T. et al., "Rapid Quantification of Adult and Developing Mouse Spatial Vision Using a Virtual Optomotor System," Invest Ophthalmol Vis Sci. (2004) 45(12):4611-4616.
Pun L, Introduction to Optimization Practice. ISBN (1969)471-70233-1.
Purpura, K. et al., "Light adaptation in the primate retina: analysis of changes in gain and dynamics of monkey retinal ganglion cells," Vis Neurosci (1990) 4(1): 75-93.
Qinghua et al., "Algorithms of Path Guidance Line Based on Computer Vision and Their Applications in Agriculture and Forestry Environment," Journal of Agricultural Machinery, Issue 3, vol. 4, Mar. 31, 2009, pp. 147-151 Abstract only.
Rolls, E.T. et al., "Role of low and high spatial frequencies in the face-selective responses of neurons in the cortex in the superior temporal sulcus in the monkey," Vision Res. (1985) 25(8):1021-1035.
Rubinstein JT et al., "How do cochlear prostheses work?", Current Opinion in Neurobiology, 1999, vol. 9, 1999, pp. 399-404.
Sambrook et al, "Molecular Cloning. A Laboratory Manual", 2d ed., Cold Spring Harbor Laboratory, New York (1989).
Sauer B., "Functional expression of the cre-lox site-specific recombination system in the yeast *Saccharomyces cerevisiae*," Mol Cell Biol. (1987) 7(6):2087-96.
Search Report issued on EP Application 15201184.7, dated Sep. 29, 2016.
Second Office Action received for Chinese Patent Application No. 201180021117.2 dated Feb. 2, 2015, 9 pages—with English translation.
Sellick PM et al., "Modulation of responses of spiral ganglion cells in the guinea pig cochlea by low frequency sound", Hearing Research, 1982, vol. 7, pp. 199-221.
Shapley, R.M. and Victor, J.D., "How the contrast gain control modifies the frequency responses of cat retinal ganglion cells." J Physiol. (1981) 318:161-79.
Sharpee, T.O. et al., "On the Importance of Static Nonlinearity in Estimating Spatiotemporal Neural Filters With Natural Stimuli," J Neurophysiol (2008) 99(5): 2496-509.
Sheridan, C., "Gene Therapy finds its niche," Nature Biotechnology (2011) 29(2):121-128.
Siegert, S., "Genetic address book for retinal cell types," Nature Neuroscience (2009) 12(9):1197-1204.
Simoncelli et al., "Characterization Of Neural Responses With Stochastic Stimuli," The Cognitive Neurosciences, 3rd edition, 327-338 (2004).
Simonelli et al., "Gene Therapy for Leber's Congenital Amaurosis is Safe and Effective Through 1.5 Years After Vector Administration," Molecular Therapy (2010) 18(3), pp. 643-650.
Sinclair, J.R. et al., "Selective ablation of a class of amacrine cells alters spatial processing in the retina," J Neurosci. (2004) 24(6):1459-67.
Sjostrand et al., "Morphometric study of the displacement of retinal ganglion cells subserving cones within the human fovea," Graefe's Arch Clin Exp Ophthalmol (1999) 237:1014-1023.
Soucy, E.R. et al., "A novel signaling pathway from rod photoreceptors to ganglion cells in mammalian retina," Neuron (1998) 21:481-493.
Stone et al., "Response properties of ganglion cells in the isolated mouse retina," Vis Neurosci (1993) 10(1): 31-39.
Strong, S.P. et al., "On the application of information theory to neural spike trains," Pac Symp Biocomput (1998) 621-32.
Third Office Action received in Chinese Patent Application No. 201180021117.2 dated Aug. 3, 2015, 8 pages with English translation.
Thyagarajan, S. et al., "Visual function in mice with photoreceptor degeneration and transgenic expression of channelrhodopsin 2 in ganglion cells," J Neurosci (2010) 30(26):8745-8758.
Tomita, H. et al., "Channelrhodopsin-2 gene transduced into retinal ganglion cells restores functional vision in genetically blind rats," Exp Eye Res (2010) 90:429-436.
Troy, J.B. et al., "Spatial properties of the cat X-cell receptive field as a function of mean light level," Vis Neurosci (1999) 16(6): 1089-1104.
Troy, J.B. et al., "Spatiotemporal integration of light by the cat X-cell center under photopic and scotopic conditions," Vis Neurosci (2005) 22(4): 493-500.
Turchinovich et al., "Non-viral siRNA delivery into the mouse retina in vivo," BMC Ophthalmology (2010) 10:25.
Ueda et al., "The mGluR6 5" upstream transgene sequence directs a cell-specific and developmentally regulated expression in retinal rod and ON-type cone bipolar cells," J Neurosci. (1997) 17(9):3014-3023.
Van Adel et al., "Delivery of ciliary neurotrophic factor via lentiviral-mediated transfer protects axotomized retinal ganglion cells for an extended period of time," Hum. Gene Ther. (2003) 14:103-115.
Victor, J.D., "The dynamics of the cat retinal X cell centre," The Journal of Physiology (1987) 386(1): 219-246.
Victor, J.D., Shapley R.M., "The nonlinear pathway of Y ganglion cells in the cat retina," J Gen Physiol. (1979) 74(6):671-689.
Volgyi, B., "Convergence and Segregation of the Multiple Rod Pathways in Mammalian Retina," J Neurosci (2004) 24(49):11182-11192.
Walther, W., Stein, U., "Viral vectors for gene transfer: a review of their use in the treatment of human diseases," Drugs (2000) 60(2):249-271.
Wang H. et al., "Efficient cochlear gene transfection in guinea-pigs with adeno-associated viral vectors by partial digestion of round window membrane", Gene Therapy, 2012, vol. 19, pp. 255-263.
Wassle H., "Parallel processing in the mammalian retina," Nat Rev Neurosci (2004) 5(10): 747-57.
Wells et al., "Optical stimulation of neural tissue in vivo," Optics Letters (2005) 30(5):504-506.
Winter, J.O. et al., "Retinal prostheses: current challenges and future outlook," J Biomater Sci Polym Ed (2007) 18(8):1031-1055.
Wohrer et al., "Virtual Retina: A biological retina model and simulator, with contrast gain control," J Comput Neurosci, vol. 26, 2009, pp. 219-249.
Wright, A.F., "Gene therapy for the eye," Br J Ophthalmol (1997) 81(8): 620-623.
Yonehara, K. et al., "Expression of SPIG1 Reveals Development of a Retinal Ganglion Cell Subtype Projecting to the Medial Terminal Nucleus in the Mouse," PLoS ONE (2008) 3(2): e1533, 18 pages.

(56) References Cited

OTHER PUBLICATIONS

Yonehara, K. et al., "Identification of Retinal Ganglion Cells and Their Projections Involved in Central Transmission of Information about Upward and Downward Image Motion," PLoS ONE (2009) 4(1): e4320, 14 pages.

Zeng, et al. "Cochlear Damage Changes the Distribution of Vesicular Glutamate Transporters Associated with Auditory and Nonauditory Inputs to the Cochlear Nucleus", The Journal of Neuroscience, Apr. 1, 2009, vol. 29, No. 13, pp. 4210-4217.

Zhang, Y. et al., "Ectopic expression of multiple microbial rhodopsins restores ON and OFF light responses in retinas with photoreceptor degeneration," J Neurosci (2009) 29(29):9186-9196.

Zierhofer CM et al., "Electronic Design of a Cochlear Implant for Multichannel High-Rate Pulsatile Stimulation Strategies", IEEE, Transactions on Rehabilitation Engineering, Mar. 1995, vol. 3, No. 1, pp. 112-116.

Zou et al., "Extraocular Image Processing for Retinal Prothesis Based on DSP," Nano/Micro Engineered and Molecular Systems (NEMS 2009), 4th IEEE International Conference on IEEE, (Jan. 2009), pp. 563-566.

Zrenner, E., et al., "Subretinal Microelectrode Arrays Allow Blind Retinitis Pigmentosa Patients to Recognize Letters and Combine them to Words," BMEI '09. 2nd International Conference on Biomedical Engineering and Informatics. Issue Date: Oct. 17-19, 2009. ISBN: 978-1-4244-4132-7. pp. 1-4.

Notification of Reasons for Rejection in JP Patent Application No. 2017-554580 dated Jun. 29, 2020 (with English translation) (4 pages).

Odo, et al., "Estimation of target's shape and position from a monocular image sequence based on visual characteristics", IEICE (The Institute of Electronics, Information and Communication Engineers) Technical Report, Jan. 17, 2002, vol. 101, No. 594, pp. 37-42.

Ahuja A. et al., "Blind Subjects Implanted With The Argus II Retinal Prosthesis Are Able To Improve Performance In A Spatial-Motor Task," British Journal Of Ophthalmology (2010).

Bach et al., "Visual Evoked Potential-Based Acuity Assessment In Normal Vision, Artificially Degraded Vision, And In Patients," British Journal Of Ophthalmology, 92:396-403 (2008).

Barranaca et a., "Sparsity and Compressed Coding in Sensory Systems," PLOS Computational Biology, Aug. 21, 2014, 32 pages.

Bi, Anding et al., "Ectopic expression of a microbial-type rhodopsin restores visual responses in mice with photoreceptor degeneration," Neuron, (Apr. 6, 2006), vol. 50, pp. 23-33.

Busskamp et al., "Genetic Reactivation Of Cone Photoreceptors Restores Visual Responses In Retinitis Pigmentosa," Science, 329:413-417 (2010).

Cardin et al., "Targeted Optogenetic Stimulation And Recording Of Neurons In Vivo Using Cell-Type-Specific Expression Of Channelrhodopsin-2," Nature Protocols, 5(2):247-254 (2010).

Chopdar A, et al., "Age Related Macular Degeneration,"—Clincial Review—British Medical Journal, 326:485-488 (2003).

Dann JF, et al., "Retinal Ganglion Cells Projecting To The Accessory Optic System In The Rat," The Journal Of Comparative Neurology, 262(1):141-158 (1987).

Eckmiller, Rolf et al., "Tunable Retina Encoders for Retina Implants: Why and How," Journal of Nueral Engineering, (2005) 2(1), pp. S91-S104.

Famulare, Michael et al., "Feature selection in simple neurons: how coding depends on spiking dynamics," Neural Comput, (2010), vol. 22, pp. 581-598.

Freund et al., "A Decision-Theoretic Generalization Of On-Line Learning And An Application To Boosting," Journal Of Computer And System Sciences, 55:119-139 (1997).

Geisler, "Visual Perception And The Statistical Properties Of Natural Scenes," Annual Review Of Psychology, 59:167-192 (2008).

Giolli RA, et al., "The Accessory Optic System: Basic Organization With An Update On Connectivity, Neurochemistry, And Function," Progress in Brain Research, 151:407-440 (2005).

Han et al., "Millisecond-Timescale Optical Control Of Neural Dynamics In The Nonhuman Primate Brain," Neuron, 62:191-198 (Apr. 30, 2009).

Huang et al., "An Optoelectronic Platform for Retinal Prosthesis," Biomedical Circuits and Systems Conference (BIOCAS 2006), IEEE, pp. 110-113, Nov. 29, 2006.

Huberman AD, et al., "Genetic Identification Of An On-Off Direction-Selective Retinal Ganglion Cell Subtype Reveals A Layer-Specific Subcortical Map Of Posterior Motion," Neuron, 62(3):327-334 (2009).

Huberman, A. et al., "Architecture and Activity-Mediated Refinement of Axonal Projections from a Mosaic of Genetically Identified Retinal Ganglion Cells." Neuron. (2008) 59(3):425-38.

Ivanova E, et al., "Evaluation Of The Adeno-Associated Virus Mediated Long-Term Expression Of Channelrhodopsin-2 In The Mouse Retina," Molecular Vision, 15:1680-1689 (2009).

Izhikevich, "Dynamical Systems In Neuroscience: The Geometry Of Excitability And Bursting," MIT Press, Cambridge, MA (2007).

Jacobs, A.L. et al., "Ruling out and ruling in neural codes." Proc Natl Acad Sci U.S.A. (2009), 106(14):5936-41.

Kawasaki et al., "Variability Of The Relative Afferent Pupillary Defect," American Journal Of Ophthalmology, 120:622-633 (1995).

Lettvin et al., "What the frog's eye tells the frog's brain." Proceedings of the Institute of Radio Engineers (1959) 47(11): 1940-51.

Liao et al., "In vivo gene delivery in the retina using polyethylenimine." BioTechniques (2007) 42:285-288.

Loewenstein JI, et al., "Outer Retinal Degeneration: An Electronic Retinal Prosthesis As A Treatment Strategy," Archives Of Ophthalmology, 122 (4):587-596 (2004).

Maguire et al., "Safety and efficacy of gene transfer for Leber's congenital amaurosis," N Eng J Med (2008) 358: 2240-2248.

Mancuso et al., "Gene therapy for red-green colour blindness in adult primates." Nature (2009) 461(7265): 784-787.

Martin et al., "Gene Delivery To The Eye Using Adeno-Associated Viral Vectors," Methods, 28:267-275 (2002).

McLaughlin, S.K. et al., "Adeno-associated virus general transduction vectors: analysis of proviral structures," J Virol. (1988) 62(6):1963-73.

Meytlis M, et al., "Assessing The Importance Of Correlated Firing Using Large Populations Of Neurons," Society For Neuroscience, Program No. 165.3 (2009).

Nirenberg S, et al, "Targeted Ablation Of Diverse Cell Classes In The Nervous System In Vivo," The Journal Of Neuroscience, 13(8):3238-3251 (1993).

Nirenberg S, et al., "Population Coding In The Retina," Current Opinion In Neurobiology, 8(4):488-493 (1998).

Nirenberg S, et al., "The Light Response Of Retinal Ganglion Cells Is Truncated By A Displaced Amacrine Circuit," Neuron, 18:637-650 (1997).

Non-Final Office Action on U.S. Appl. No. 15/073,002 dated Mar. 1, 2017 (093873-1095).

Norcia et al., "Measurement Of Spatial Contrast Sensitivity With The Swept Contrast VEP," Vision Research, 29(5):627-637 (1989).

Norcia, A.M., and Tyler, C.W., "Spatial frequency sweep VEP: visual acuity during the first year of life," Vision Res. (1985) 25(10):1399-408.

Pandarinath et al., "A Novel Mechanism For Switching A Neural System From One State To Another," Frontiers In Computational Neuroscience, 31(4):2 (2010), p. 1-18.

Pandarinath et al., "Symmetry breakdown in the ON and OFF pathways of the retina at night: functional implications," J Neurosci (2010) 30(30): 10006-10014.

Paninski, et al. "Statistical models for neural encoding, decoding, and optimal stimulus design", Progress in Brain Research, vol. 165, 2007, pp. 493-507.

Paninski, L., "Maximum likelihood estimation of cascade point-process neural encoding models," Network: Comput Neural Syst. 15(2004), pp. 243-262.

Panzeri et al., "Correcting For The Sampling Bias Problem In Spike Train Information Measures," Journal Of Neurophysiology, 98(3):1064-1072, Review (2007).

(56) References Cited

OTHER PUBLICATIONS

Perry VH et al., "Functional lamination in the ganglion cell layer of the macaque's retina", Neuroscience, vol. 25, No. 1, 1988, pp. 217-223.

Petersen-Jones et al., "AAV Retinal Transduction In A Large Animal Model Species: Comparison Of A Self-Complementary AAV2/5 With A Single-Stranded AAV2/5 Vector," Molecular Vision, 15:1835-1842 (2009).

Piedade, Moises et al., "Visual Neuroprothesis: A Non Invasive System for Stimulating the Cortex," IEEE Transactions on Circuits and Systems—I: Regular Papers, (Dec. 2005), vol. 53, No. 10, pp. 2648-2662.

Pillow, et al. "Spatio-Temporal Correlations And Visual Signalling In A Complete Neuronal Population," Nature 454(7207):995-999 (2008).

Prusky et al., "Rapid Quantification Of Adult And Developing Mouse Spatial Vision Using A Virtual Optomotor System," Investigative Ophthalmology & Visual Science, 45(12):4611-4616 (2004).

Pun, Introduction to Optimization Practice, ISBN 471-70233-1 (1969).

Purpura K, et al. "Light Adaptation In The Primate Retina: Analysis Of Changes In Gain And Dynamics Of Monkey Retinal Ganglion Cells," Visual Neuroscience 4(1):75-93 (1990).

Rolls ET, et al., "Role Of Low And High Spatial Frequencies In The Face Selective Responses Of Neurons In The Cortex In The Superior Temporal Sulcus In The Monkey," Vision Research, 25(8):1021-1035 (1985).

Shapley RM, et al., "How The Contrast Gain Control Modifies The Frequency Responses Of Cat Retinal Ganglion Cells," The Journal Of Physiology, 318:161-179 (1981).

Sheridan, "Gene Therapy Finds Its Niche," Nature Biotechnology, 29(2):121-128 (2011).

Simoncelli et al., "Characterization of neural responses with stochastic stimuli," The Cognitive Neurosciences, 3rd edition (2004), 20 pages.

Simonelli et al., "Gene Therapy For Leber's Congenital Amaurosis Is Safe And Effective Through 1.5 Years After Vector Administration," Molecular Therapy, 18(3):643-650 (2010).

Sjostrand et al., "Morphometric Study Of The Displacement Of Retinal Ganglion Cells Subserving Cones Within The Human Fovea," Graefe's Archive Clinical Experimental Ophthalmology 237:1014-1023 (1999).

Troy JB, et al., "Spatial Properties Of The Cat X-Cell Receptive Field As A Function Of Mean Light Level," Visual Neuroscience, 16(6):1089-1104 (1999).

Troy JB, et al., "Spatiotemporal Integration Of Light By The Cat X-Cell Center Under Photopic And Scotopic Conditions," Visual Neuroscience, 22(4):493-500 (2005).

Ueda et al., "The mGluR6 5" Upstream Transgene Sequence Directs A Cell-Specific And Developmentally Regulated Expression In Retinal Rod And ON-Type Cone Bipolar Cells," The Journal Of Neuroscience, 17(9):3014-3023 (1997).

Victor JD, et al., "The Nonlinear Pathway Of Y Ganglion Cells In The Cat Retina", Journal Of Genetic Physiology, 74(6):671-689 (1979).

Walther W, et al., Viral Vectors For Gene Transfer: A Review Of Their Use In The Treatment Of Human Diseases, Drugs, 60(2):249-271, Review (2000).

Wassle, "Parallel Processing In The Mammalian Retina," National Review Of Neuroscience Journal, 5(10):747-757 (2004).

Wright, "Gene Therapy For The Eye," British Journal Of Ophthalmology, 81(8):620-622, Review (1997).

Zhang Y, et al., "Ectopic Expression Of Multiple Microbial Rhodopsins Restores ON And OFF Light Responses In Retinas With Photoreceptor Degeneration," The Journal Of Neuroscience, 29 (29):9186-9196 (2009).

Zou, Yuexian et al., "Extraocular Image Processing for Retinal Prothesis Based on DSP," Nano/Micro Engineered and Molecular Systems (NEMS 2009), 4th IEEE International Conference on IEEE, (Jan. 2009), pp. 563-566.

Zrenner et al., "Subretinal Microelectrode Arrays Allow Blind Retinitis Pigmentosa Patients To Recognize Letters And Combine Them To Words," Biomedical Engineering And Informatics (BMEI) '09. 2nd International Conference On Biomedical Engineering and Informatics, ISBN: 978-1-4244-4134-1. pp. 1 013 4 (2009).

Office Action issued in Chinese Patent Application No. 201680032611.1, dated Jul. 26, 2019.

Notice of Allowance issued in co-pending U.S. Appl. No. 16/056,308, dated Sep. 12, 2019.

Asaga Ryohei, et al., "Age estimation from a face image using Gabor feature", ITE (The Institute of Image Information and Television Engineers) Technical Report, Japan, The Institute of Image Information and Television Engineers (ITE), Aug. 22, 2011 (10 Pages).

Dang-Hui Liu et al., "Sampling Gabor Features for Face Recognition", International Conference on Neural Networks and Signal Processing, 2003., U.S.A., IEEE, Dec. 14, 2003, pp. 924-927.

Odo Satoru, Hoshino Kiyoshi, "Estimation of target's shape and position from a monocular image sequence based on visual characteristics", IEICE (The Institute of Electronics, Information and Communication Engineers) Technical Report, Japan, The Institute of Electronics, Information and Communication Engineers (IEICE), Jan. 17, 2002, vol. 101, No. 594,pp. 37-42.

Office Action in JP 2021-019858 dated Feb. 15, 2022 (with English Translation) 8 pages.

Notice of Allowance on U.S. Appl. No. 17/011,651, dated Apr. 27, 2022.

Decision of Final Rejection on JP 2021-019858 dated Jun. 6, 2022.

Kinoto Hideki and Akamatsu Shigeru, "Building a real-time facial expression recognition system based on a combination of features from the static face image and image sequence", ITE (The Institute of Image Information and Television Engineers) Technical Report vol. 31, No. 14, pp. 89-92, Japan, The Institute of Image Information and Television Engineers (ITE), Feb. 24, 2007.

Notice of Preliminary Rejection on KR 10-2017-7033316 dated Jun. 23, 2022.

* cited by examiner

MACHINE VISION WITH DIMENSIONAL DATA REDUCTION

CROSS REFERENCE TO RELATED APPLICATIONS

This application is a continuation of U.S. patent application Ser. No. 15/567,407, filed Oct. 18, 2017, which is the U.S. National Stage of International Patent Application No. PCT/US2016/028406, filed Apr. 20, 2016, which claims priority under 35 U.S.C. § 119 to U.S. Provisional Patent Application No. 62/150,068, filed Apr. 20, 2015, the entire contents of these applications are incorporated herein by reference in their entirety. This application also incorporates by reference U.S. Provisional Application Nos. 61/527,493 (filed Aug. 25, 2011), 61/657,406 (filed Jun. 8, 2012), 61/308,681 (filed on Feb. 26, 2010), 61/359,188 (filed on Jun. 28, 2010), 61/378,793 (filed on Aug. 31, 2010), 61/382,280 (filed on Sep. 13, 2010), and Ser. No. 13/230,488, (filed on Sep. 12, 2011). This application also incorporates by reference International Patent Application No. PCT/US2011/026526 (filed on Feb. 28, 2011) and PCT/US2011/049188 (filed Aug. 25, 2011) referred herein as the "Prosthesis Applications," International Patent Application No. PCT/US2012/052348 (filed Aug. 24, 2012) referred to herein as the "Machine Vision Application." The contents of each of the forgoing applications are incorporated by reference in their respective entireties.

BACKGROUND

The following description is provided to assist the understanding of the reader. None of the information provided or references cited is admitted to be prior art. Machine vision (or computer vision) refers to technology that allows a machine (e.g., a computer) to use visual information to, for example, extract information from an image, to solve some task, or to "understand" the scene in either a broad or limited sense. In general, machine vision is concerned with the extraction of information from image data. The image data can take many forms, such as single images, video sequences, views from multiple cameras, or higher dimensional data (e.g., three dimensional images from a medical scanner). Several approaches have been proposed for developing image data pre-processing schemes for machine vision based on abstract models of the operations of the visual system, but their effectiveness is limited. There remains much room for improving machine vision such that it can be more effective and practical.

SUMMARY

The foregoing summary is illustrative only and is not intended to be in any way limiting. In addition to the illustrative aspects, embodiments, and features described above, further aspects, embodiments, and features will become apparent by reference to the following drawings and the detailed description.

In an illustrative, a method is described that includes receiving, by a processing device, raw image data corresponding to a series of raw images, and processing the raw image data with an encoder of the processing device to generate encoded data. The encoder is characterized by an input/output transformation that substantially mimics the input/output transformation of at least one retinal cell of a vertebrate retina. The method also includes processing, by the processor, the encoded data to generate dimension reduced encoded data by applying a dimension reduction algorithm to the encoded data. This latter dimension reduction algorithm is configured to further compress the information contained in the encoded data to make it useful for machine vision algorithms. Specifically, this additional compression allows features to be pulled out of the encoded data—features that are useful for machine vision, but are not available in the original raw images.

In addition, in some implementations, the features produced by the additional dimension reduction may be built up to produce feature signatures. A feature signature includes information related to a plurality of encoded image regions. A feature signature may, through the plurality of encoded image regions, carry information that is greater (i.e., more descriptive) than its component features. For example, in some embodiments, a feature pulled out by applying the dimension reduction to the encoded data may include speed information including a specific kind of speed information that is not confounded by different lighting conditions and environments. The plurality of regions in the signature may be a set of regions that corresponds to regions of a human's body. The feature signature in this example can be generated by creating a vector whose components are the speeds in the individual regions (i.e., the speeds associated with motion of the individual body parts, as measured using the encoded data). Note that, as mentioned above, by using the encoded data, rather than the raw image, speed can be calculated in each region without being confounded by other factors, such as the lighting conditions or environment in which the person is moving, etc. This vector, this signature, can then be used to identify the person, i.e., distinguish him or her from others, as the signature captures many identifying features of a person's body movements, such as gait, heat tilt, relative sizes of body parts, etc. Similarly, the plurality of regions or sectors could correspond to regions of objects, allowing humans or other living beings to be distinguished from nonliving, i.e., rigid, beings.

In some implementations, the encoded data may be represented as one or a series of encoded images (often referred to as a series of retinal images or encoded retinal images), and processing the encoded data includes processing the encoded series of retinal images to generate features or feature signatures. As above, the feature signatures may include information related to a plurality of retinal image regions.

In some implementations, processing the encoded data includes applying a trained algorithm to the encoded data. The trained algorithm may include a convolutional neural network (CNN). The trained algorithm may have been trained on a training data set of encoded training data, and the encoded training data may have been encoded using a training encoder that is characterized by an input/output transformation that substantially mimics the input/output transformation of one or more retinal cells of a vertebrate retina. In a further implementation, the training set of encoded training data includes encoded images of a virtual environment, and the raw image data includes raw images of a real environment. The training set of encoded training data may include images acquired under a first set of conditions, and the raw image data may include raw images acquired under a second set of conditions different from the first. The first set of conditions and the second set of conditions may include different lighting conditions.

In another implementation, the method may include applying a machine vision algorithm to the dimension reduced encoded data. Processing the encoded data to generate dimension reduced encoded data may be performed after the processing the raw image data to generate encoded data and before the applying the machine vision algorithm to the dimension reduced encoded data. Processing the raw image data to generate encoded data may include generating encoded data that is dimensionally reduced relative to the raw image data, and processing the encoded data to generate the dimension reduced encoded data may include additionally compressing the encoded data that is already dimensionally reduced relative to the raw image data. The amount of information contained in the encoded data may be compressed by a factor of at least about 2 relative to the corresponding raw image data, and the dimension reduced encoded data may be compressed by a factor of at least about 2 relative to the corresponding encoded data. The amount of information contained in the encoded data may be compressed by a factor of at least about 10 relative to the corresponding raw image data, and the dimension reduced encoded data may be compressed by a factor of at least about 10 relative to the corresponding encoded data.

In another implementation, an apparatus includes at least one memory storage device configured to store raw image data, and at least one processor operatively coupled with the memory. The processor is programmed to receive the raw image data corresponding to a series of raw images and process the raw image data to generate encoded data using an input/output transformation that substantially mimics the input/output transformation of at least one retinal cell of a vertebrate retina. The processor is further programmed to process the encoded data to generate dimension reduced encoded data by applying a dimension reduction algorithm to the encoded data. The dimension reduction algorithm may be configured to compress an amount of information contained in the encoded data. The apparatus may further include a robotic device operatively coupled to the at least one processor, wherein the robotic device comprises at least one image sensor configured to generate the raw image data.

In another implementation, a non-transitory computer-readable medium having computer-executable instructions that, upon execution by a computing device, cause the computing device to perform operations including receiving raw image data corresponding to a series of raw images, processing the raw image data to generate encoded data using an input/output transformation that substantially mimics the input/output transformation of at least one retinal cell of a vertebrate retina, and processing the encoded data to generate dimension reduced encoded data by applying a dimension reduction algorithm to the encoded data. The dimension reduction algorithm is configured to compress an amount of information contained in the encoded data.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
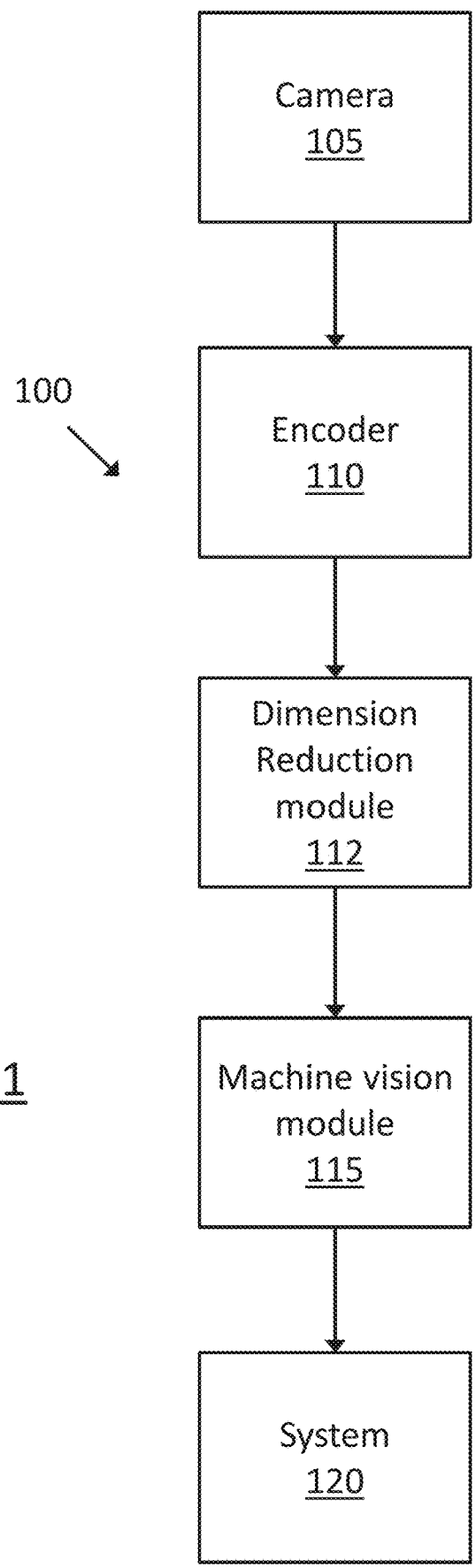
FIG. 1 is a block diagram of a device with machine vision in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Machine vision has numerous applications, ranging from relatively simple tasks, such as industrial systems used to count objects passing by on a production line, to more complicated tasks such as facial recognition, and perceptual tasks (e.g., to allow robots to navigate complex environments). A non-limiting list of examples of applications of machine vision include systems for controlling processes (e.g., an industrial robot or an autonomous vehicle), detecting events (e.g., for visual surveillance or people counting), organizing information (e.g., for indexing databases of images and image sequences), modeling objects or environments (e.g., industrial inspection, medical image analysis or topographical modeling), and interaction (e.g., as the input to a device for computer-human interaction).

In some applications, machine vision can involve highly computationally expensive tasks. A single color digital image may be composed of millions of pixels or more. Each pixel can have an associate value such as a multiple (e.g., 8 or 24) bit value defining the coordinates of the pixel in a color space (e.g., the familiar RGB color space, the YCbCr space, the HSV space, etc.). Video streams may include sequences of such images at frame rates of, e.g., dozens of frames per second, corresponding to bit rates of hundreds of megabits per second or more. Many machine vision applications require quick processing of such images or video streams (e.g., to track and react to the motion of an object, to identify or classify an object as it moves along an assembly line, to allow a robot to react in real time to its environment, etc.) for the machine vision to be practical.

Processing such a large volume of data under such time constraints can be extremely challenging. In some embodiments, techniques are used for processing image data that reduces the raw amount of information. In such embodiments, the techniques can also retain (or even accentuate) the features of the image data that are salient for the machine vision task at hand. The pre-processed image data, rather than the raw data, can be input to a machine vision system including a machine learning algorithm, thereby allowing the algorithm to learn features of the image that were difficult or impossible to learn before. This reduces the processing burden on the system, making learning tractable and allowing for speedy response and potentially improved performance.

The retina of the vertebrate eye provides this kind of image processing. That is, the retina of the vertebrate eye can take in a visual stimulus and convert the stimulus into a form that can be understood by the brain. This system (developed over the course of millions of years of evolution) is highly efficient and effective, as evidenced by the high level of complex visual perception in mammals (particularly monkeys and humans).

Some approaches for developing image data pre-processing schemes for machine vision based on abstract models of the operations of the vertebrate visual system can be based on rough approximations to the actual performance of the retina, but these have not been highly effective.

The visual world is extremely complex. Human brains are continuously flooded with visual signals, and yet the signals are rapidly parsed and utilized. One reason for such speed is the dimension reduction performed by the retina. Millions of years of evolution have shaped the retina into a powerful dimension-reduction system. The vertebrate visual system takes visual input, pulls out what is needed and discards the rest. If this dimension reduction were harnessed, the capabilities of machine vision would be greatly increased.

As discussed in the Machine Vision Application, we have developed a model of retinal input/output relations that performs this dimension reduction. It stands apart from other retina models in that it generalizes to stimuli of arbitrary complexity (faces, landscapes, people walking, etc., see the Machine Vision Application and the Prosthesis Applications). What the model does is collapse (also referred to herein as compress) the amount of information that exists in the visual world into a tractable form. The collapsed form can then be used as the input to other algorithms including machine learning and machine vision algorithms (both known in the art and described in present disclosure). The collapsed form makes it possible for the algorithms to learn the visual environment and perform tasks with it in a strikingly more effective way than is possible when the algorithms rely directly on the normal, raw, high-dimensional visual input In the present disclosure, we describe applications of this approach to an array of tasks, including navigation, face recognition, person recognition, object recognition, emotion/expression recognition, trend recognition in economic/geological/weather, etc. data, disease detection (e.g., using medical images such as MRI images, CT scan images, pathology slides, etc.) and other recognition/detection tasks performed well by animals or humans.

In the Machine Vision Application, we demonstrated the effectiveness of the approach in applications including navigation tasks, as this is particularly challenging (requires processing in both space and time). We used as the environment a virtual reality 3-D environment constructed using an open source Panda 3D graphics package. The learning algorithm used was from a "deep learning" family, specifically, a convolutional neural network (CNN). We compared the performance of the navigator under two conditions: when it used the normal raw images as its input and when it used images that were filtered through the retina model (i.e. the encoder). We refer to the first as the "pixel navigator" and the second as the "retina navigator." As shown for example in International App. No. PCT/US2012/052348 (see, e.g., FIGS. 10 and 11), performance was substantially better (many fold better) when the learning algorithm used the latter—the algorithm extracted the relevant features from the visual environment, and very importantly, the learning generalized to other environments (rural, suburban, different lighting conditions, etc.), issues that have been highly problematic for artificial systems.

In the present disclosure we described techniques that, in some embodiments, exhibit some or all of the following advantages: 1) translating the power of the dimension-reduction approach to a real world environment, and 2) adding additional dimension-reduction methods, both biologically-inspired and artificial, to create new algorithms for face recognition, person recognition, object recognition, emotion/expression recognition, trend recognition in economic/geological/weather, etc. data, and other recognition/detection tasks performed well by animals or humans.

In one aspect, a method is disclosed including: receiving raw image data corresponding to a series of raw images; processing the raw image data with an encoder to generate encoded data, where the encoder is characterized by an input/output transformation that substantially mimics the input/output transformation of one or more retinal cells of a vertebrate retina; and processing the encoded data to generate dimension reduced encoded data by applying a dimension reduction algorithm configured to compress amount of information contained in the encoded data.

Various implementations may include any of the above described devices, techniques, and elements thereof, either alone or in any suitable combination.

Following below are more detailed descriptions of various concepts related to, and implementations of, methods and systems for teaching a target language. The various concepts introduced above and discussed in greater detail below may be implemented in any of numerous ways, as the described concepts are not limited to any particular manner of implementation. Examples of specific implementations and applications are provided primarily for illustrative purposes.

In some embodiments, an encoder can be used that provides a near-complete replication of the operations performed by the retina. As described in detail in the various international patent applications incorporated by reference above (henceforth the "Prosthesis Applications"), such an encoder may be used to develop a highly effective retinal prosthetic. In some embodiments, the encoder is applied to machine vision.

When used as a preprocessing step (in particular, a dimension-reduction step or dimension-shifting), an encoder can substantially enhance the performance of machine vision algorithms. In some embodiments, the encoder can allow the machine vision algorithm to extract information effectively in a broad range of environments and lighting conditions. In cases in which existing machine vision algorithms are partly effective, a dimension reduction may serve as a strong enhancer. The encoder may allow the extraction to be carried out more effectively (leading to, e.g., higher performance) as well as faster and more efficiently.

The data output by the encoder may be further processed by using another dimension reduction algorithm. The additional processing can be done prior to (or as a part of) the application of a machine vision algorithm. This additional dimension reduction algorithm may be biologically inspired or partially or entirely artificial. As discussed in the machine vision application, the encoder converts raw images into new representations, e.g., retina encoded images. These new representations are representations that were not present in the raw images. The representations may be advantageously utilized for further dimensional reduction processing which allows for more effective and efficient processing of the original raw image data. Accordingly, the additional dimensional reduction algorithms may be applied to the retina encoded images (including the additional features or representations included therein). Note that the retina encoded images are fundamentally different from the raw images and thus the dimension reduction performed on them leads to features (or parameters) for machine learning that have not been produced before and cannot be produced by applying dimension reduction processes directly to the raw images (e.g., the encoder creates novel patterns that evolve in time; since the patterns are produced by neuronal responses to images and not the images themselves, the parameters chosen to capture the patterns are different from those that might be used to capture features of raw images).

In some embodiments, a learning algorithm (e.g., a machine vision algorithm) may be trained on data (e.g., images) that have been processed using the retinal encoder and one or more additional dimension reduction processes. As described, e.g., in the examples provided herein, the inventor has found that, in a wide variety of applications, algorithms trained on such processed data sets (as opposed to, e.g., raw image data) exhibit enhanced performance. Further, the inventor has found that the enhanced performance is highly generalizable. That is, the various algorithms perform well even when presented with input (e.g., images) generated under significantly different conditions (e.g., lighting conditions, environmental color palette, etc.) than those found in the training images. In some cases the inventor has found that algorithms trained on virtual images (e.g., images generated based on a virtual rendering of an environment) that have been processed using the techniques described herein perform well even when presented with real world environments that are significantly different from the virtual training environment.

As shown in the examples provided herein, training data sets that are processed using the techniques described herein (e.g., featuring retinal encoding followed by one or more additional dimension reduction processes) can provide an enhanced training environment for a broad range of learning algorithms including machine vision algorithms for navigation, facial identification, body identification, etc.

Some embodiments can employ a retinal encoding process of the type described in detail in the Prosthesis Applications. Such embodiments can include a device that receives a stimulus and transforms the stimulus into a set of codes with a set of encoders. The device can also transform the codes into signals using an interface. The signals can activate a plurality of retinal cells with a high-resolution transducer. Activation of the plurality of retinal cells can result in retinal ganglion cell responses to a broad range of stimuli, which can be substantially similar to the time dependent responses of retinal ganglion cells from a mammalian retina responding to the same stimuli. Encoders used in such devices may be adapted to process image data for use in machine vision applications and are not necessarily limited to retinal prosthetics.

A retina prosthesis described in the Prosthesis Applications, like the normal retina, can be an image processor. The retina prosthesis can extract essential information from received stimuli and can reformat the information into patterns of action potentials that the brain can understand. The patterns of action potentials produced by a mammalian retina are in the retina's code or the ganglion cell's code. The retina prosthesis can convert visual stimuli into this same code, or a close proxy of it, so that the damaged or degenerated retina can produce normal or near-normal output. Because the retina prosthesis uses the same code as the normal retina or a close proxy of it, the firing patterns of the ganglion cells in the damaged or degenerated retina are the same as (or substantially similar to) firing patterns of normal ganglion cells. Thus, such a prosthetic can allow the retina to send to the brain the same (or substantially similar) as the normal retina signals indicating the visual world.

As discussed in the Prosthesis Application, the encoders can use input/output models for retinal cells. The input/output models can be generated using data obtained from studies of the input/output response of mammalian retinal cells to a variety of stimuli, e.g., both white noise (WN) and natural scene (NS) movies. In some embodiments, the encoders can be based on a linear nonlinear cascade model that includes a spatiotemporal transformation characterized by a plurality of parameters. Such parameters can be optimized based on data obtained through experiments using the mammalian retina. Use of the parameters can result in an artificial process that closely mimics the response of the mammalian cells to a broad range of stimuli. The result can be a model that captures the input/output relations for natural images (static or spatiotemporally-varying), such as faces, landscapes, people walking, children playing, etc. The model can also capture the input/output relation for white noise stimuli or stimuli with Gaussian statistics.

Some embodiments can leverage data obtained through experiments. Accordingly, the generated encoders can accurately simulate retinal processing without requiring a detailed abstract understanding of the retina's underlying processing schemes. For example, it is believed that retinal processing in primates and humans highlights features in the visual stimulus useful for pattern recognition tasks (e.g., facial recognition) while de-emphasizing or eliminating other features (e.g., redundant information or noise) to allow for efficient processing in the brain. As of yet, there is no complete abstract understanding of the details of this processing scheme, which developed as the result natural selection over the course of eons. Nevertheless, despite such a lack of abstract understanding, the devices and techniques described herein can capture the benefit of this processing, by accurately mimicking the retinal response.

In other words, in various embodiments described herein, the models or modules can be data-driven. The models or modules can be a data-driven model of retinal input/output relations and provide realistic image pre-processing. The models or modules can output to downstream machine vision algorithms a signal that has been pre-processed. The pre-processing step can accomplish the same (or substantially similar) kind and the same (or substantially similar)

magnitude of dimension reduction as the biological retina. Thus, such models or modules can offer the same advantages as the mammalian retina.

In various embodiments, the retinal processing operates to reduce the total amount of information from the raw image data while retaining salient features for a given application. The reduction in total amount of information can be efficient, in a way that is analogous to the way a mammalian retina achieves efficiency. Such a process is referred to herein as "dimension reduction" or "biological dimension reduction (BDR)." For example, in some embodiments, even though the total amount of information in the retinal encoded data is reduced, the machine vision algorithm may exhibit better performance when the retinal encoded data is reduced than if the machine vision algorithm received raw image data. The better performance is the result of, essentially, providing the machine vision algorithm with the most important information received by the retina and reducing or discarding some information which is less important to a particular task of the machine vision algorithm.

In various embodiments, the retinal encoded data may be a compressed form of the raw visual data (e.g., received by the retina) by a factor of at least 1.5, at least 2, at least 3, at least 4, at least 5, or more, e.g., in the range of 1-100 or any subrange thereof. The compression can correspond to a dimension reduction produced by the encoders. For example, in some embodiments, the bit rates of the retinal encoders may be quantified and can be compared to the entropy of the raw image data used as stimulus by the encoder (also measured in bits per unit time), and the ratio taken to determine a compression ratio. For example, in some cases described in the Prosthesis applications, an encoder is described with a bit rate of 2.13 bits/s compared to an input raw data bit rate of 4.9 bits/s. Thus, the data compression produced by the encoders was in this example nearly 7-fold.

As described herein some embodiments may include applying additional dimension reduction algorithms (biologically inspired, artificial, or a combination thereof) to the encoded data. In various embodiments, the dimension reduced retinal encoded data may be further compressed by a factor of at least 1.5, at least 2, at least 3, at least 4, at least 5, or more, e.g., in the range of 1-100 or any subrange thereof. In some embodiments, this compression corresponds to a dimension reduction produced by the additional processing of the encoded data. For example, in some embodiments, the bit rates of the post-processing encoded data may be quantified and can be compared to the bit rate of the pre-processing encoder output, and the ratio taken to determine a compression ratio.

FIG. 1 is a block diagram of a device 100 with machine vision in accordance with an illustrative embodiment. In alternative embodiments, device 100 may have additional, fewer, or different elements. Further, the use of arrows in FIG. 1 is not meant to be limiting with respect to the order of elements. Device 100 includes a camera 105, an encoder 110, a machine vision module 115, and a system 120. In some embodiments, the system 120 can be controlled, at least in part, by the machine vision module. Camera 105 receives visual stimulus and converts it to digital image data. In some embodiments, the digital image data can be a stream of digital images. This digital image data may be referred to herein as a "raw" image data. Raw image data may include any image data prior to processing by a retinal encoder.

In some embodiments, encoder 110 can receive the image data and processes the image data using one or more retinal encoders. In some embodiments, the retinal encoders can be of the type described herein and/or in the Prosthesis Applications. The encoder 110 can convert the received image data into a format that is the same as (or substantially similar to) a format output by a mammalian retina. The output of the encoder 110, referred to as encoded retinal image data, is passed to a dimension reduction module 112. The dimension reduction module 112 processes the output from the encoder 110 to provide additional dimension reduction beyond any dimension reduction performed by the encoder 110. For example, the dimension reduction module 112 may receive a stream of encoded retinal images from the encoder 110 and generate dimension reduced encoded data. In other words, the encoder 110 creates the encoded retinal image data by encoding information from the raw images. The dimension reduction module 112 uses features from the encoded retinal image data for various machine vision tasks. The dimension reduction module 112 uses only a subset of the features represented by the encoded retinal image data as needed for a specific machine vision task and ignores the features unnecessary for the specific machine vision task.

The output of the dimension reduction module 112 is passed to the machine vision module 115. The machine vision module 115 can process the data by using one or more machine vision techniques known in the art and/or described herein. The machine vision module 115 can generate an output that that may be used for any suitable purpose. As shown in FIG. 1, the output of the machine vision module 115 can be sent to one or more systems 120. In some embodiments, system 120 can be a robotic system. In some embodiments the image processing and/or control may be performed in real time or near real time.

The system shown in FIG. 1 is meant to be exemplary only, and various other types of machine vision systems may be used. For example, in some embodiments, the controlled system 120 may not be included. For example, the output of the machine vision module 115 can be stored for further processing rather than used directly for control. In some embodiments, camera 105 may be replaced by a source of stored image data. For example, camera 105 may be replaced by a storage device that stores digital video. In some embodiments additional elements may be included in device 100 such as various processors, controllers, user controls, input or output devices, etc.

In some embodiments, the dimension reduced encoded data can also be built up to generate feature signatures. Feature signatures include information related to a plurality of encoded retinal image regions or sectors. A feature signature may, through the plurality of image regions, carry information that is greater and more descriptive than its component features. In some implementations, feature signatures may allow the identification or classification of, for example, people, faces, and objects, using relatively simple features extracted from the encoded data such as lateral motion, rate of lateral motion, vertical motion, rate of vertical motion, density, on-off rate, among other features in the encoded data. A vector can be created whose components are the values of the features in the individual regions (e.g., the rate of lateral motion in each region, as measured using the encoded data). This vector, this signature, can then be used to perform machine vision tasks. For example, for face recognition, the regions in the signature (the components in the vector) correspond to the regions in a face (e.g., the region covering the left eyebrow, the regions covering the left eye, etc.). If the feature is, for example, the rate of lateral motion (i.e., lateral speed), then the vector captures several identifying characteristics of individual faces such as relative movement of the eyebrows and eyes. Such vectors can be used to distinguish among faces and among emotions produced by faces. Further detail is provided below where the illustrative embodiments (FIGS. 7-9) are described in "Example 2—Visual Tasks." Similarly, the plurality of regions or sectors could correspond to regions of the body (e.g., the head, the upper arm, the lower arm, etc.). If the feature is, again, the rate of lateral motion, then a vector can capture several identifying characteristics of a person's body, such as gait, head tilt, relative sizes of body parts, etc. Such vectors can be used to distinguish among people. Again, further detail is provided below in the detailed descriptions of FIGS. 7-9 in "Example 2—Visual Tasks." Likewise, the plurality of regions can also correspond to regions of objects, allowing humans or other living beings to be distinguished from nonliving, e.g., rigid, beings. The plurality of regions can also correspond to regions of moving scenes, such that the signature captures a global property, e.g., optic flow. Note that since the encoded data can contain a series of images (movies of encoded data), the signatures can be vectors of time series data, as shown in the figures.

In various embodiments, camera 105 may be any device capable of converting visual stimulus to a digital form (e.g., a stream of digital images). Various embodiments may include cameras 105 based on charge-coupled devices (CCDs); active pixel sensors (APS) such as complimentary metal-oxide-semiconductor (CMOS) sensors, thin-film transistors (TFTs), or arrays of photodiodes; and combinations thereof.

Each of the digital images generated by camera 105 may include at least 0.01 megapixels, at least 0.1 megapixels, at least 1 megapixel, at least 2 megapixels, or more, for example, in the range of 0.01-1000 megapixels or any subrange thereof. The stream of digital images may be characterized by a frame rate (e.g., the number of image frames per second) of at least 10 Hz, at least 50 Hz, at least 100 Hz, or more, for example, in the range of 1-1000 Hz or any subrange thereof. The digital images may be color, grayscale, black and white, or other suitable types of images.

In some embodiments, camera 105 can be based on a charge-coupled device (CCD). In one embodiment, the camera 105 can be a Point Grey brand model Firefly MV image capture device (capable of capturing images with 752×480 pixels with 8 bits/pixel at 60 frames per second). In another embodiment, camera 105 can be an e-con Systems brand model e-CAM50 OMAP GSTIX image capture device. The camera 105 can integrate an OmniVision brand model OV5642 camera module, which is capable of capturing images with 1280×720 pixels with 8 bits/pixel at 30 frames per second.

In some embodiments, images can be acquired by camera 105 and transmitted to the encoder 110 with sufficient speed to allow device 100 to operate without undesirable lag times. In some embodiments, a high bandwidth connection can be provided between camera 105 and the encoder 110. For example, a data transfer of greater than 20 MB/sec can be achieved using a Universal Serial Bus (USB) 2.0 interface between camera 105 and the encoder 110. In other embodiments, a parallel interface can be used between camera 105 and the encoder 110, such as the parallel interface integrated into the camera image signal processor on the Texas Instruments brand OMAP 3530 model processor. In various embodiments, other suitable connections may be used, including wired or wireless connections. Camera 105 can be interfaced with the encoder 110 using any connection capable of high speed data transfer, including, but not limited to, serial interfaces, such as Institute of Electrical and Electronics Engineers (IEEE) standard 1394, USB 2.0, USB 3.0, USB 3.1, etc.; parallel interfaces; analog interfaces, such as National Television System Committee (NTSC) standard or phase alternating line (PAL) standard; or a wireless interface. In some embodiments, camera 105 can be integrated onto the same circuit board as the encoder 110.

The encoder 110 can process an image stream using the techniques described herein, including, for example, implementing encoders that convert images into codes, mimicking the operation of retinal circuitry. That is, the encoder 110 can receive an image and output a data stream that is the same as (or substantially similar to) a data stream output by a mammalian retina given the same image. The transformations implemented by the encoders can be applied to the series of input images, producing an encoded output. For example, the encoded output may be in the form of values similar to the firing rates of retinal cells that would have been generated had the images been received by a mammalian retina. In some embodiments, the output of the encoder 110 can also be, for example, information mimicking the generator potential of the retinal cells. The generator potential can be the output of a linear component of the retinal model (the output of the convolution of the input image with the linear filters). The encoded output of the encoder 110 may be a pulse train of spikes or pulses that would be generated by mammalian retinal cells if the mammalian retinal cells were stimulated with the same input image.

In some embodiments, sets of different encoders 110 may be used to mimic processing by a mammalian retina. There are different types of retinal output cells in a mammalian retina, and various encoders 110 can be used to replicate the different types of mammalian retinal output cells. Differences may correspond to a particular cell type (e.g., "on" cells or "off" cells) or to the cell position on the retina (e.g., "on" cells in the central retina and "off" cells in the retina's periphery). In embodiments in which device 100 has more than one encoder 110, the encoders 110 can operate in parallel, either independently or through at least one or more coupling mechanisms.

Figure 2:
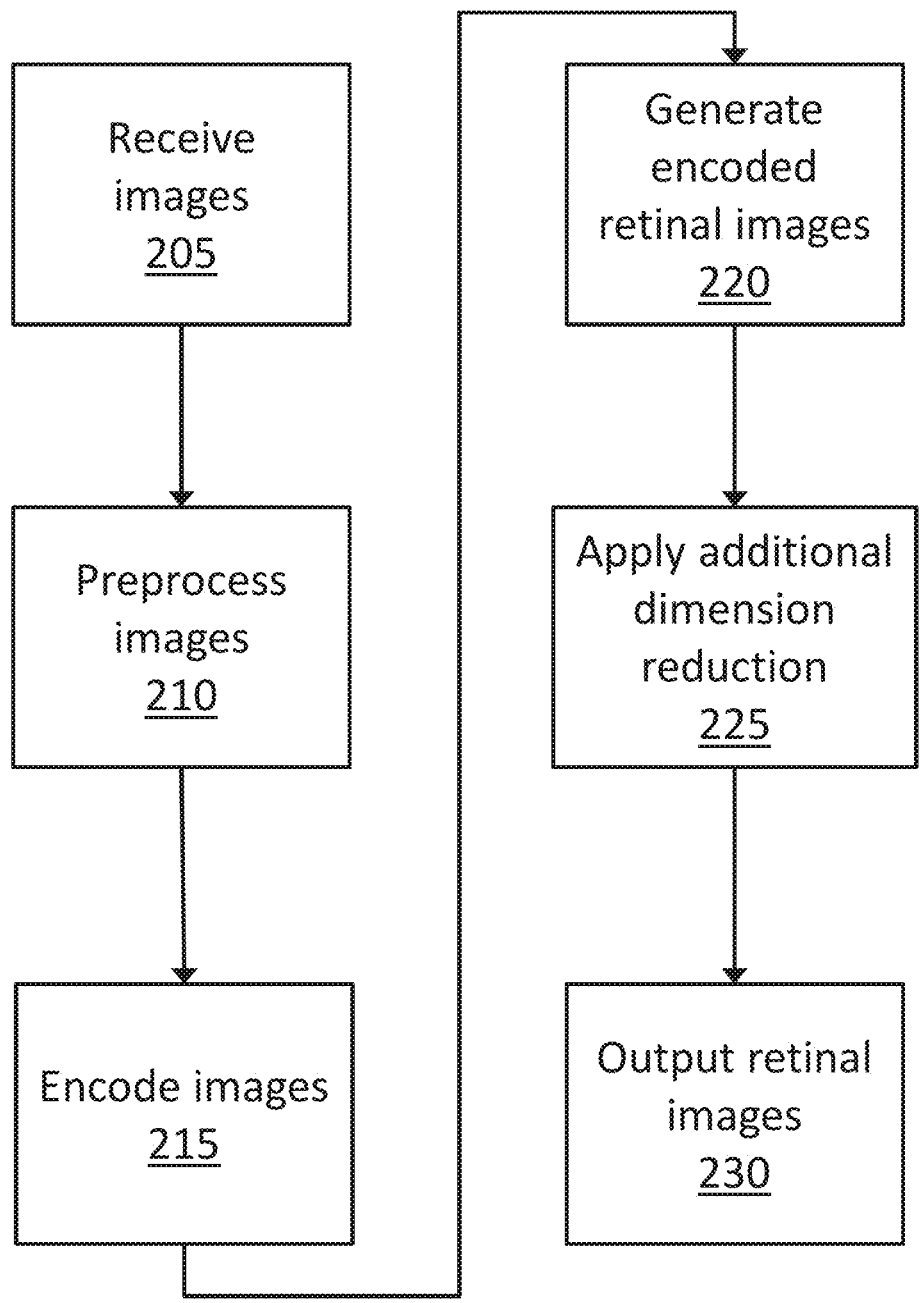
FIG. 2 is a flow chart illustrating the operation of an encoder module in accordance with an illustrative embodiment.

FIG. 2 is a flow chart illustrating the operation of an encoder module 110 in accordance with an illustrative embodiment. In alternative embodiments, fewer, additional, and/or different operations may be performed. Also, the use of a flow diagram is not meant to be limiting with respect to the order of operations performed. In an operation 205, the encoder module 110 can receive one or more images. In some embodiments, the one or more images can be received from camera 105 (or some other suitable source). In operation 210, the one or more images can be pre-processed. For example, the one or more images can be pre-processed to rescale the contrast and/or intensity of the one or more images, to apply a noise filter to the one or more images, to crop the one or more images, etc. In some embodiments, operation 210 may not be performed.

In an operation 215, the one or more images can be encoded. The one or more images can be processed in a way that mimics a mammalian retinal cell response to the images. For example, in one embodiment, for various positions in the image field, the one or more images can be input and a time dependent value corresponding to a firing rate that would have been generated by a mammalian retinal cell (or group of cells) if the one or more images were processed by a mammalian retina can be output. In an embodiment, the firing rate output is formatted as follows: for a given time t, the output is a matrix of bits where the element at position (x,y) corresponds to the firing rate of the retinal cell at position (x,y).

In some embodiments, the operation 215 may include generating information mimicking the response of a mammalian retinal cell using a metric other than firing rate. For example, the output of the encoders could correspond to the activation state of the cell, the intracellular potential, the generator potential mentioned above, etc.

In an operation 220, the encoded information from operation 215 can be used to generate one or more encoded retinal images. In some embodiments, the encoded retinal images can be suitable for processing by the machine vision module 115. For example, where the encoded information is output as a matrix of firing rates, as described above, a firing rate retinal image may be generated, where the intensity of each pixel in the encoded retinal image is determined by the firing rate value of a corresponding element in the matrix (see FIG. 3 for an example). Any suitable relationship between firing rate and pixel intensity may be used, including a linear relationship, a non-linear relationship, a polynomial relationship, a logarithmic relationship, etc. Operation 220 can include converting a pixel intensity to a firing rate using any suitable technique including the use of a look-up table. In some embodiments, the firing rate may be represented in the encoded retinal image using an image characteristic other than intensity. For example, in an embodiment in which the encoded retinal images are color images, a color space coordinate of each pixel can correspond to the firing rate.

In an operation 225, the encoded retinal images undergo additional dimension reduction processing, which may include processing the one or more encoded retinal images to generate dimension reduced encoded data. The dimension reduced encoded data may be built up to produce feature signature data, as discussed above and also in further detail below in the descriptions of FIGS. 7-9.

Additional processing may also be applied to the encoded retinal images, including rescaling, filtering, cropping, smoothing, etc.

In an operation 230, the one or more retinal images can be output to the machine vision module 115. The one or more retinal images can be output using any suitable method, which can be wired or wireless. In some embodiments, the retinal images can be output similar to how a mammalian retina outputs retinal images.

EXAMPLES

Example 1—Navigation Processor

The Machine Vision Application describes a navigator that is effective in a virtual reality environment. However, according to an example of the present disclosure a navigator can also be effective in a real world environment. Accordingly, various embodiments of the present disclosure can be used in multiple environments and multiple applications.

For example, a mobile robot called the Turtlebot can be used. The Turtlebot is an open source personal robot designed for robotics development and testing. The Turtlebot runs on the Robot Operating System (ROS), which facilitates hardware and communication mechanisms and brings together data from sensors and hardware components on the robot into a single software framework. The robot includes a 3-wheeled circular locomotive base from Yujin Robot called iClebo Kobuki, a Microsoft Kinect sensor that includes a camera, and an on-board factory-calibrated gyro for better sensor input and state estimation of the robot. A laptop is placed on-board the robot and processes all sensor data on-the-fly to make online, real-time decisions. The laptop runs a Linux operating system (Ubuntu) and ROS one-layer beneath to control and process all robot data on the laptop.

Such an example, however, is only one specific implementation of the present disclosure. Other embodiments can include additional, fewer, or different elements. For example, a generic embodiment can include a locomotive element, a visual sensing element (e.g., a camera), and a processing element configured to receive data from the visual sensing element and provide instructions to the locomotive element.

In one testing condition, the Kinect's three-dimensional camera system was ignored and only the two-dimensional color camera was used. Accordingly, the decisions made by software of the device were based on two-dimensional images. The software of the device was configured to receive input images from the camera. The input images were divided into 7 regions by the device. The software determined the speed of each region and in which of twelve categories each region fit into. The software then chose the region with the slowest speed and directed the device to travel in the direction of the slowest region.

The process described above allows a device to navigate an environment with few or no collisions. In Example 1, similar front-end software was used as was used in the virtual navigation task described in the Machine Vision Application. That is, a similar training set that allowed the virtual navigator to determine speeds in the virtual world was used to determine speeds in the real environment in Example 1. In Example 1, changes to the software included modifications to the steps subsequent to the speed determination and small changes in the navigation rules relevant to the framework of the device's shape in a confined, real-world space. Specifically, the software decides whether to move forward or to turn by accumulating data for all pairs of frames during the time between decisions (e.g., 29 pairs of frames over a 1 second period) and determining which of the seven regions had the slowest speed over all the frame pairs.

That is, the device made a decision whether to turn or to continue forward once a second. Each second, the camera captured twenty-nine images. Each image was divided into seven regions. The speed of each region is determined by comparing the region of the most recent captured image with the corresponding region of the previously captured image. The device then determines which of twelve categories the speed of each region falls into (e.g., A-L, with A being the slowest and L being the fastest). The device tallies the speed categories corresponding to each region and determined which of the seven regions had the most tallies in the lowest category since the last decision. For example, for regions 1-7 and categories A-L, if the left-most region 1 had one tally in category A and the rest of the tallies in categories B-L, and no other region had any tallies in category A, the device determined to turn in the direction of region 1. In another example, if the left-most region 1 had two tallies in category B and the rest of the tallies in categories C-L and the right-most region 7 had one tally in category B and the rest of the tallies in categories C-L, the device determined to face region 1. By averaging all of the pairs of frames since the last decision, a more stable decision is made.

Figure 3A:
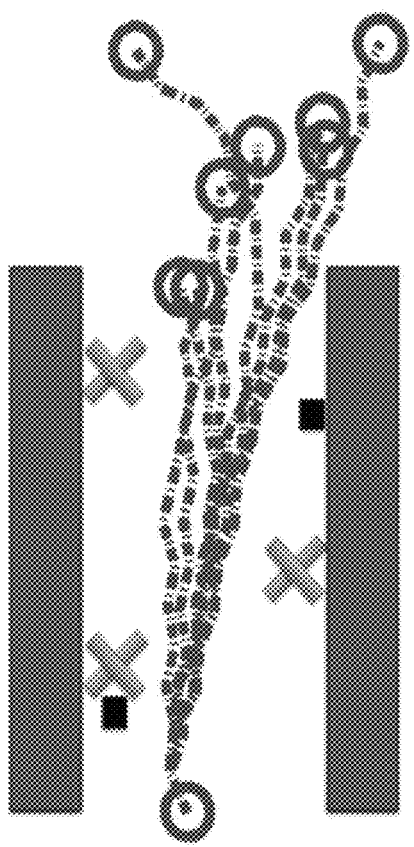
FIG. 3A depicts trajectories of a robot navigating through a real-world environment controlled by an example retina navigator in accordance with an illustrative embodiment.
Figure 3B:
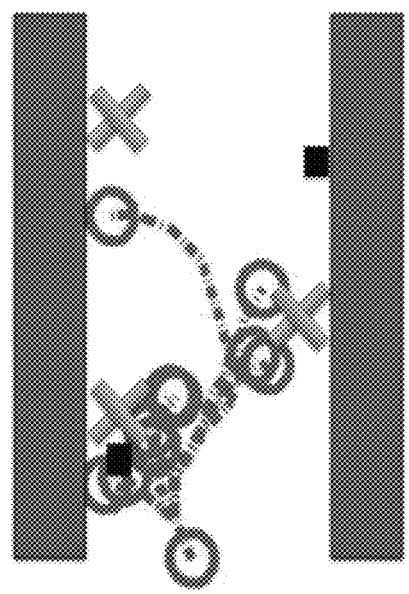
FIG. 3B depicts trajectories of a robot navigating through a real-world environment controlled by an example pixel navigator in accordance with an illustrative embodiment.

FIGS. 3A and 3B show the performance of the device of Example 1 navigating through a real-world environment according to an illustrative embodiment. FIG. 3A shows the performance of the device using a "retina navigator." FIG. 3B shows the performance of the device using a "pixel navigator." The device's girth is indicated by the diameter of the circle in the figure. As shown in FIGS. 3A and 3B, the girth of the device is relatively large and the device has to maneuver well to avoid collisions with walls and obstacles, where Xs indicate chairs and black squares indicate wastepaper baskets. In both cases, the robot moved forward at 0.4 meters per second (m/s).

FIG. 3A shows the trajectories of the device when it was controlled by a "retina navigator." A retina navigator can be a navigator described in the Machine Vision Application, which learned speeds in its visual environment from movies filtered through the retina model (e.g., the dimension-reduced visual world). The dimension-reduced retina model can be a model consistent with the processes described with relation to FIGS. 1 and 2 above.

FIG. 3B shows the trajectories of the device when it was controlled by a "pixel navigator." A pixel navigator can be a navigator described in the Machine Vision Application that learned speeds in its visual environment from unfiltered movies (e.g., movies not dimension-reduced by the retina model). In both cases (shown in FIGS. 3A and 3B), the navigators were trained in a Panda-3 virtual environment. In other embodiments, a different virtual environment can be used to train the navigators.

As shown in FIG. 3A, when the device was controlled by the retina navigator, the device maneuvered through the obstacles in the real environment without running into a wall or an obstacle. In contrast, as shown in FIG. 3B, when the device was controlled by the pixel navigator, the device crashed into walls and obstacles. In no case was the device able to make it through the course.

In a different version of the example shown in FIGS. 3A and 3B, the device used the retina navigator described above. The device was then initiated on a path in an open room towards a standing person. As the device approached the standing person, the device detected that a collision would occur on the current trajectory and turned to avoid the standing person. When the person moved to be in the trajectory of the device, the device again turned to avoid colliding with the person. This process was repeated several times, and each time, the device turned to avoid colliding with the person.

Another example includes devices with software as explained above. In one version, a retina navigator was used, filtering the input images as discussed above with reference to FIGS. 1 and 2. In another version, a pixel navigator was used, in which no filtering of the input images was performed. Each navigator was trained using the same images. Each navigator was then run in various virtual environments that differed from the environment used to train the navigators. For example, the virtual environment used during training was a replica of a rural environment. Each navigator was then placed in the rural virtual environment, and the navigators performed similarly, navigating well through the environment and rarely running into obstacles. The retina navigator made it through the obstacle course about 95% of the time while the pixel navigator made it through the obstacle course about 90% of the time.

However, when the navigators were placed in different environments with different lighting conditions without a re-training, the different navigators performed differently. The retina navigator had relatively straight trajectories and rarely ran into obstacles and had a similar performance as the navigators in the rural environment. However, the pixel navigator had disorganized trajectories (seemingly random) and often ran into obstacles. In the three different environments, the retina navigator made it through the obstacle course about 90% to 95% of the time. However, the pixel navigator made it through the obstacle course about 0% to 25% of the time.

Figure 4:
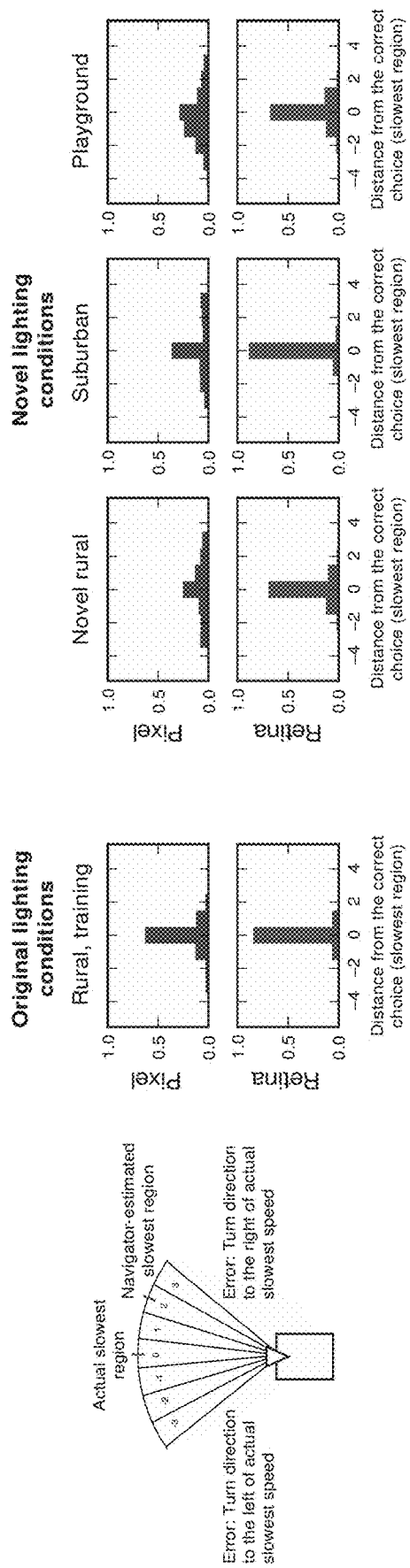
FIG. 4 depicts histograms of the results of the retina navigator and the pixel navigator through different environments in accordance with various illustrative embodiments.

FIG. 4 shows histograms of the results of the retina navigator and the pixel navigator through the different environments. The diagram to the left of FIG. 4 illustrates how correct decisions of the slowest region are determined. As described above, each image is divided into seven regions, each region being a vertical strip of the image. In the example shown in the diagram at the left of FIG. 4, the middle region is the region with the slowest movement. Thus, if a navigator determines that, for example, the second region to the right of the middle region is the slowest region, that decision receives a score of +2 on the graphs to the right of FIG. 4. Accordingly, in such a situation, the navigator will move to face the right-hand direction when it should have kept straight on.

The left-most graph of FIG. 4 shows histograms of the correct decisions made by the pixel navigator (on the top) and the retina navigator (on the bottom) in the rural environment (similar to the training environment). As shown, the retina navigator made more correct decisions (decisions with a score of 0) and fewer incorrect decisions (decisions different than 0) than the pixel navigator. But, compared to the graphs to the right of FIG. 4, the retina navigator and the pixel navigator performed similarly. The graphs on the right-hand side of FIG. 4 show histograms illustrating the number of correct decisions made by the pixel navigator (on the top) and the retina navigator (on the bottom) in three environments different than the rural environment and with different lighting conditions than the rural environment. As shown in FIG. 4, the retina navigator made a similar number of correct decisions when placed in the different environments as it did when placed in the rural environment. However, the pixel navigator made more and larger errors in the different environments than it did in the rural environment. Accordingly, the retina image processing described with regard to FIGS. 1 and 2, above, greatly improved the performance of the devices with no image processing.

Figure 5:
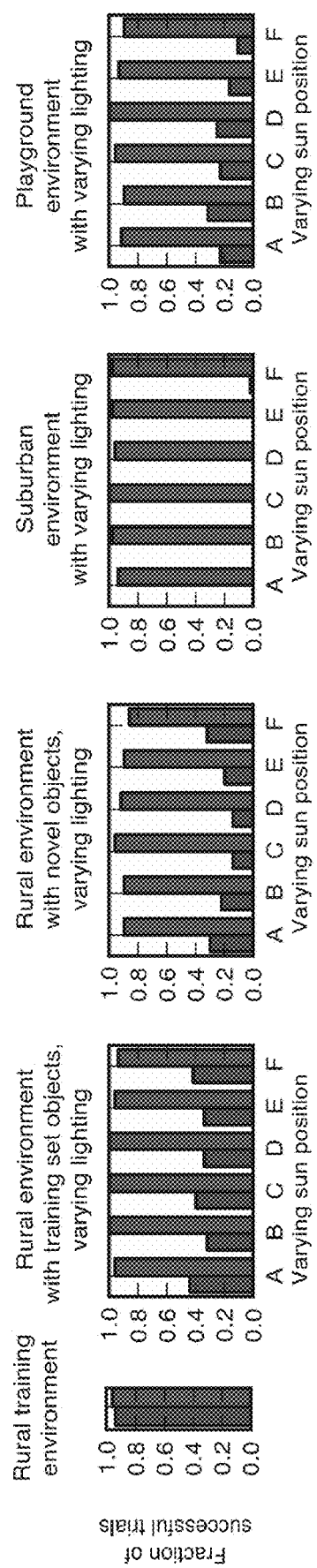
FIG. 5 depicts graphs indicating how well the retina navigator and the pixel navigator performed in various environments with various lighting conditions in accordance with illustrative embodiments.

FIG. 5 shows graphs indicating how well the retina navigator and the pixel navigator performed in various environments with various lighting conditions in accordance with an illustrative embodiment. The left-most graph of FIG. 5 shows the fraction of times that the pixel navigator (left bar) and the retina navigator (right bar) successfully made it through an obstacle course in the rural environment with the lighting conditions that both navigators were trained on. As shown in the graph, both navigators made it through the course more than 90% of the time. The various other graphs shows the fraction of times that the pixel navigator (left bars) and the retina navigator (right bars) successfully made it through various environments (rural with training objects, rural with novel objects, suburban, and playground) under various lighting conditions (i.e., the sun in position A-F, where position of the sun was 30°, 40°, 50°, 90° (straight overhead), 150°, and 160° from the left). As shown in the graphs, the pixel navigator rarely made it through to the end of the course. Indeed, the best performance by the pixel navigator was slightly over 40% of the time, and that was using the testing rural environment, but with different obstacles. In the other environments, the pixel navigator did poorly. However, the retina navigator successfully made it through the course over 90% of the time in all environments and all lighting conditions.

Figure 6A:
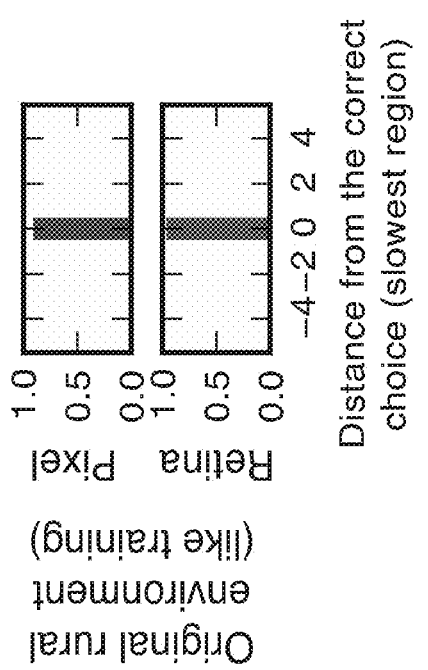
FIGS. 6A-6E depict histograms of correct decisions made by a pixel navigator and a retina navigator various environments with various lighting conditions in accordance with illustrative embodiments.
Figure 6B:
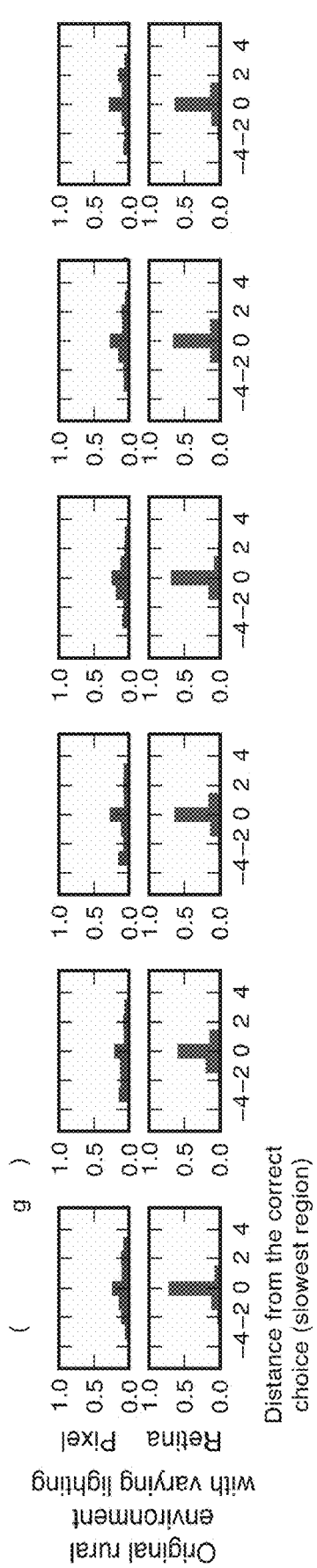
Figure 6C:
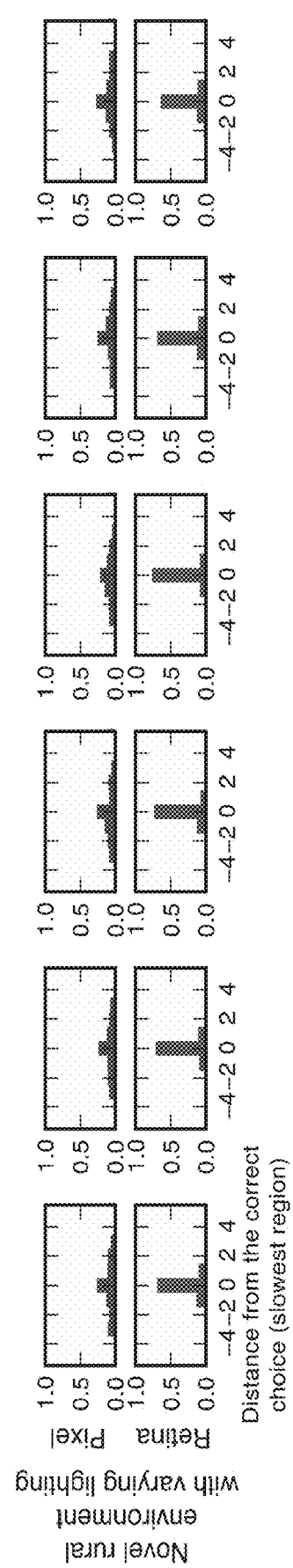
Figure 6D:
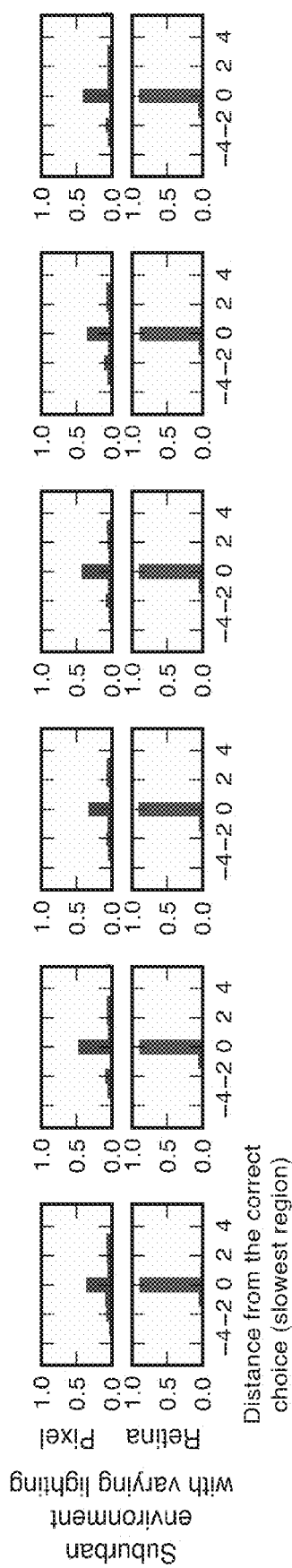
Figure 6E:
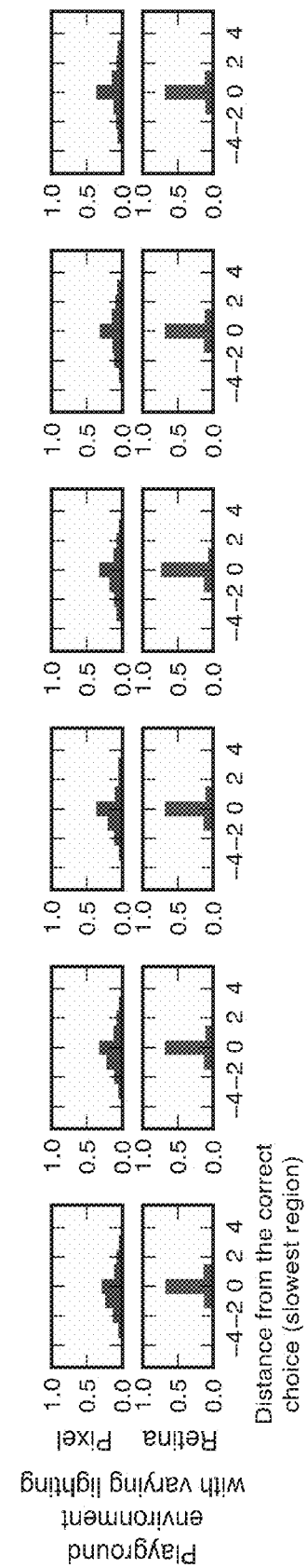

Similar to the graphs shown in FIG. 4, the graphs of FIGS. 6A-6E show histograms of the results of the retina navigator and the pixel navigator through the various environments with various lighting conditions. FIG. 6A shows a histogram of the correct decisions made by the pixel navigator (on the top) and the retina navigator (on the bottom) in the rural environment with the same lighting conditions as the training environment. FIGS. 6B-6E show histograms of the correct decision made by the pixel navigator and the retina navigator in the various environments with various lighting conditions. As shown in the various histograms, the pixel navigator made more and larger errors (non-zero scores) than the retina navigator in environments different than the training environment.

In sum, FIGS. 3A, 3B, 4, 5, and 6A-E show that the dimension-reduction of the retina (or in this application, the encoder) can allow a machine learning algorithm to learn features that can be universally useful for visual tasks such as navigation. The results show that the features learned in one training set allowed a navigator to maneuver through space very effectively in many environments, including real world environments.

The dimension reduction of the retina or the encoder can also allow machine learning algorithms to learn features that appear to be universally useful for other tasks, such as face recognition, person recognition, object recognition, emotion/expression recognition, trend recognition in economics, geology, weather, etc., data, disease detection (e.g., using medical images such as MRI images, CT scan images, pathology slides, etc.) and other recognition/detection tasks performed well by animals or humans. For the sake of clarity, the encoder performs the initial dimension reduction and then one or more additional dimension reduction steps is then performed (on the encoded data), either as a separate step or as a step incorporated into the machine learning process, to pull out features. In some embodiments, a given feature or set of features can be built up from a plurality of regions in the encoded images; the built up features can produce feature signatures. The feature signatures can identify faces, objects, emotions, etc., as described above and shown in the various figures throughout.

Example 2—Visual Tasks

As mentioned above, the methods described in the Machine Vision Application allow machine learning algorithms to learn features of the visual world efficiently and in a generalized way. Such methods achieve this by reducing the dimensionality of the visual input (e.g., using retinal encoding). This application focuses on applying one or more additional dimension reduction processes to the encoded data in such a way that the machine learning algorithms (e.g., convolutional neural networks, or CNNs), when searching parameter space (e.g., finding the weights in a CNN), find general solutions, rather than falling into local solutions (e.g., as a result of local minima in parameter space).

For example, in various embodiments, the solution for a given training data set may be a set of weights that captures a transformation (or computation or mapping). A dimension reduced training set may allow the algorithm to find a solution that generalizes to multiple problems. That is, the trained algorithm can extract useful information (or perform a task) from various sources of visual information. The algorithm can perform well when presented with image sets from a single sample (e.g., a training set) and when presented with out-of-sample image sets (e.g., image sets from different environments, under different lighting conditions, etc.).

For example, in the case of the virtual navigator, a visual input was passed through the encoder, also referred to as the virtual retina. The encoded data was then divided into 7 regions, and each region was passed into the CNN. The CNN was then trained to extract a feature, the average speed, in each region. The speed of each region was categorized as one of twelve categories. The CNN was trained to determine the speed by minimizing the error between its output and the true speed, which could be ascertained directly from a Panda 3D virtual environment. The weights that emerged in the CNN as a result of this training were general and had accurate estimates of speed in completely new environments (e.g., completely new visual input that had also been dimension-reduced by the encoder and the additional dimension reduction step in the same way).

In some instances, as described in Example 1 above, the result of such a training can be generalized to apply to different environments including images of real world environments that differed significantly from the virtual training environment (e.g., completely different objects, and lighting conditions, etc.).

In various embodiments, the principles described above may be used to provide tools for machine vision.

In some embodiments, the dimension reduction provided by the encoder can be a starting point, and other dimension reductions (biologically inspired or otherwise) can be combined with it.

Dimension reductions of the encoded data involving lateral or vertical motion, speed, mean firing rate, flicker rate, are examples that can be used this way. These features are potentially valuable for capturing people, objects, data, etc. Thus, in various embodiments, using dimension reduction methods (first of the raw images by the encoder and then further dimension reductions on the encoded data to extract features and generate feature signatures) can allow numerous machine visual tasks to be performed, such as navigation, person recognition, face recognition, object recognition, emotion/expression recognition, trend recognition in economics, geology, weather, etc., data, disease detection (e.g., using medical images such as MRI images, CT scan images, pathology slides, etc.) and other recognition and/or detection and/or classification tasks performed well by animals or humans.

Figure 7:
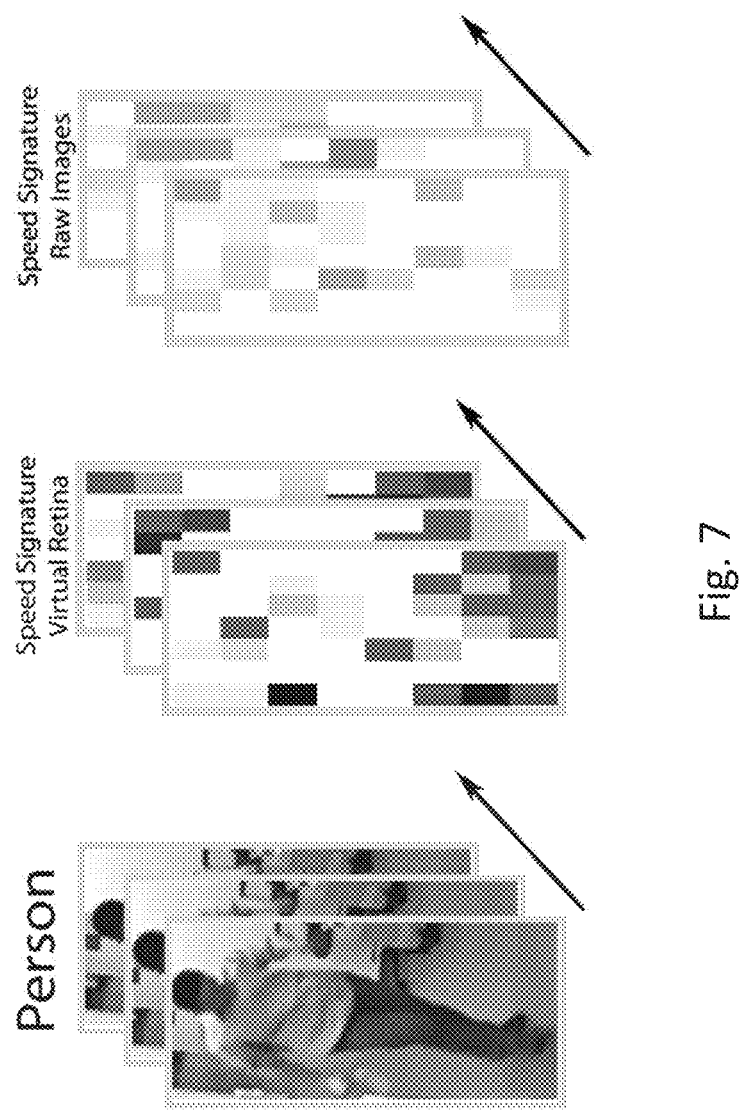
FIG. 7 depicts stages of human recognition in a video according to an illustrative embodiment.

FIG. 7 illustrates stages of person recognition in a video according to an illustrative embodiment. In one embodiment, region or sector speed can be used as a tool for person recognition. In an example embodiment, a training set of 3,500 videos of people walking were preprocessed by the encoder, also referred to as the virtual retina (VR), as described above. The output of the encoder was converted back into video, divided into grids (as shown in FIG. 7), and input into the CNN. The CNN made speed estimates for each grid region, as discussed above.

The speed signatures of FIG. 7 include vectors with a speed component. In the example of FIG. 7, the body of the person was converted into a vector with 48×N components, where 48 was the number of regions in the grid, and N was the number of pairs of frames from which speed was measured. In various embodiments, other suitable numbers of grid elements and pairs or frames may be used.

Figure 8:
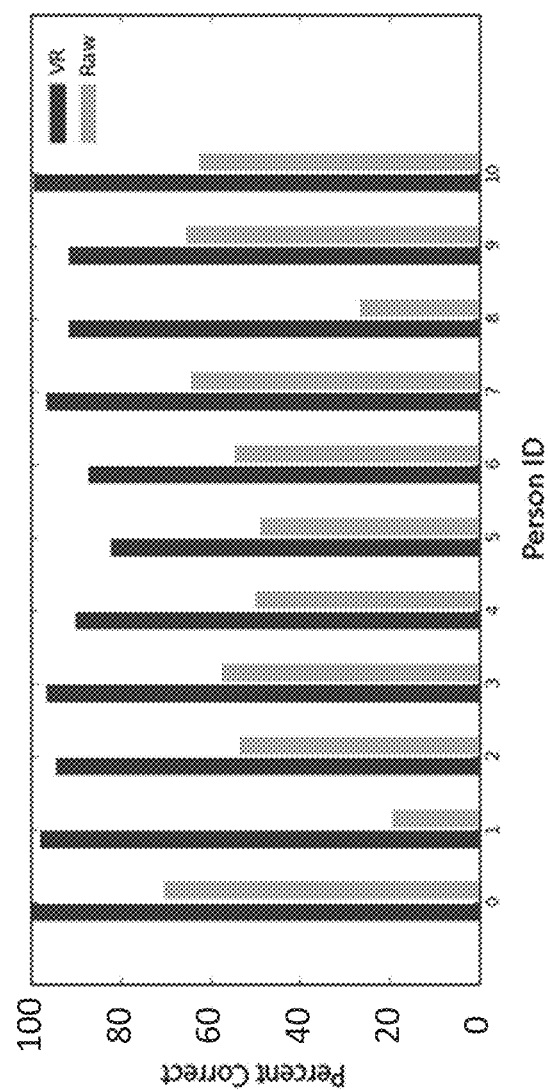
FIG. 8 depicts a histogram of the effectiveness of a convolutional neural network in recognizing a person using an encoded image (referred to here as a virtual retina image (VR)), and raw image data in accordance with an illustrative embodiment.

In some embodiments, the speed signatures can be used to recognize individuals. FIG. 8 shows a histogram of the effectiveness of the CNN to recognize a person using the encoded data (the virtual retina data) and using raw image data. Using the Euclidean (e.g., two-dimensional) distance between speed signatures, it is possible to correctly match an individual in a video clip to the same individual in another clip. Such a matching can be "person recognition."

FIG. 8 shows the results of an example of person recognition using the speed signatures of 3,500 video clips containing eleven different people. The speed signatures were of the full body of people walking. The speed signatures were evaluated by a CNN and the CNN was tasked with identifying a person based on the speed signatures. For each trial, a reference clip of the 3,500 clips was chosen and the CNN compared the speed signature of the reference clip to the speed signatures of the other 3,499 clips. The speed signature of the other 3,499 clip that was most similar to the speed signature of the reference clip was chosen by the CNN. The chosen clip was then compared to the reference clip to determine if the chosen clip and the reference clip contained the same person walking. FIG. 8 shows the percent correct for each of the eleven people. For each person, the percent correct using the encoded data (the data produced by the virtual retina) is shown as the left-hand bar and the percent correct using the raw image data is shown as the right-hand bar. Using the virtual retina, the CNN correctly matched the reference clip to a clip that contained the same person about 90% of the time. However, as shown in FIG. 8, when the raw image data was used, the CNN had a much lower success rate.

Figure 9:
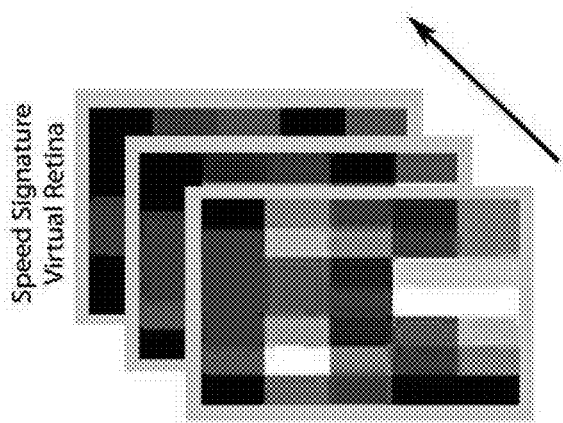
FIG. 9 depicts an example use of an encoded image (referred to here as virtual retina image (VR)), to create a motion signature of a person's face in accordance with an illustrative embodiment.
Figure 9:
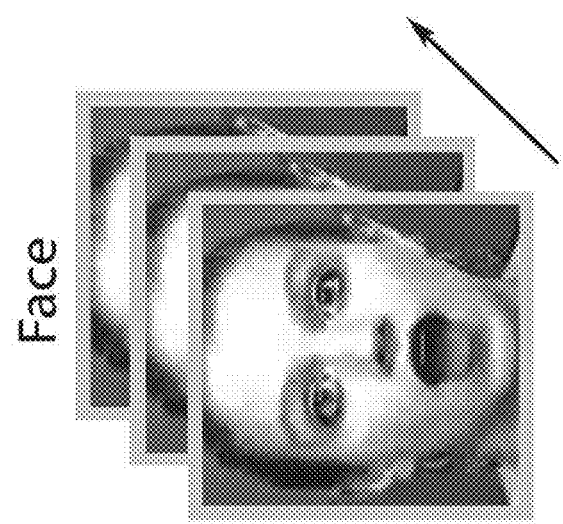

Bodies, objects, faces, animated data (weather maps, economic data, etc.) have moving parts, and the movements can be exploited to capture movements in both space and time. FIG. 7 shows an example using full-body images of a person walking. FIG. 9 shows an example of using a virtual retina to create a motion signature of a person's face. The size of the grids can be chosen so that each region in the grid has movement largely in one direction. For example, for full-body images (such as those in FIG. 7.), an upper arm can move in one direction, a lower arm can move in another direction, etc. For face images, an eyebrow can move in one direction, a lower lip can move in another direction, etc. By choosing grid sizes that capture mostly movement in a single direction, the CNN can readily capture speed in each region. The direction of motion is implicitly captured in the speed signature because the body parts or face parts move in time (e.g., the upper arm moves in a certain direction relative to the other body parts, and this is contained in the vector components). Thus, a great deal about a person's physical being can be contained in such a signature. The direction of movement of the component parts, the relative movement of the component parts, and the natural flow of motion in time and space from one region of a grid to another for physical, (typically) solid, objects. Thus, using such signatures allows the information required for identification to be captured with a relatively small number of parameters (e.g., the parameters that make up the speed signature).

In various embodiments, such an approach can be implemented in a number of forms. For example, speed of various regions can be extracted using a CNN. In other embodiments, other learning networks such as a support vector machine can be used. In yet other embodiments, other fixed methods such as an optical flow algorithm (e.g., the Fahrenback algorithm) can be used. In various embodiments, various parameters can be modified, such as the number of grid regions, size and shape of grid regions, number of frames in video clip, number of frames for estimating speeds, number of speeds estimated, etc. The metric used to compare speed signatures can also be modified. In some examples discussed above, Euclidean distance was measured. However, some alternatives to measuring Euclidean distance include distances determined by deep learning classifiers, Bayesian classifiers, support vector machines, Lebesgue space ($L^p$) distances, the Mahalanobis distance, etc.

Figure 10:
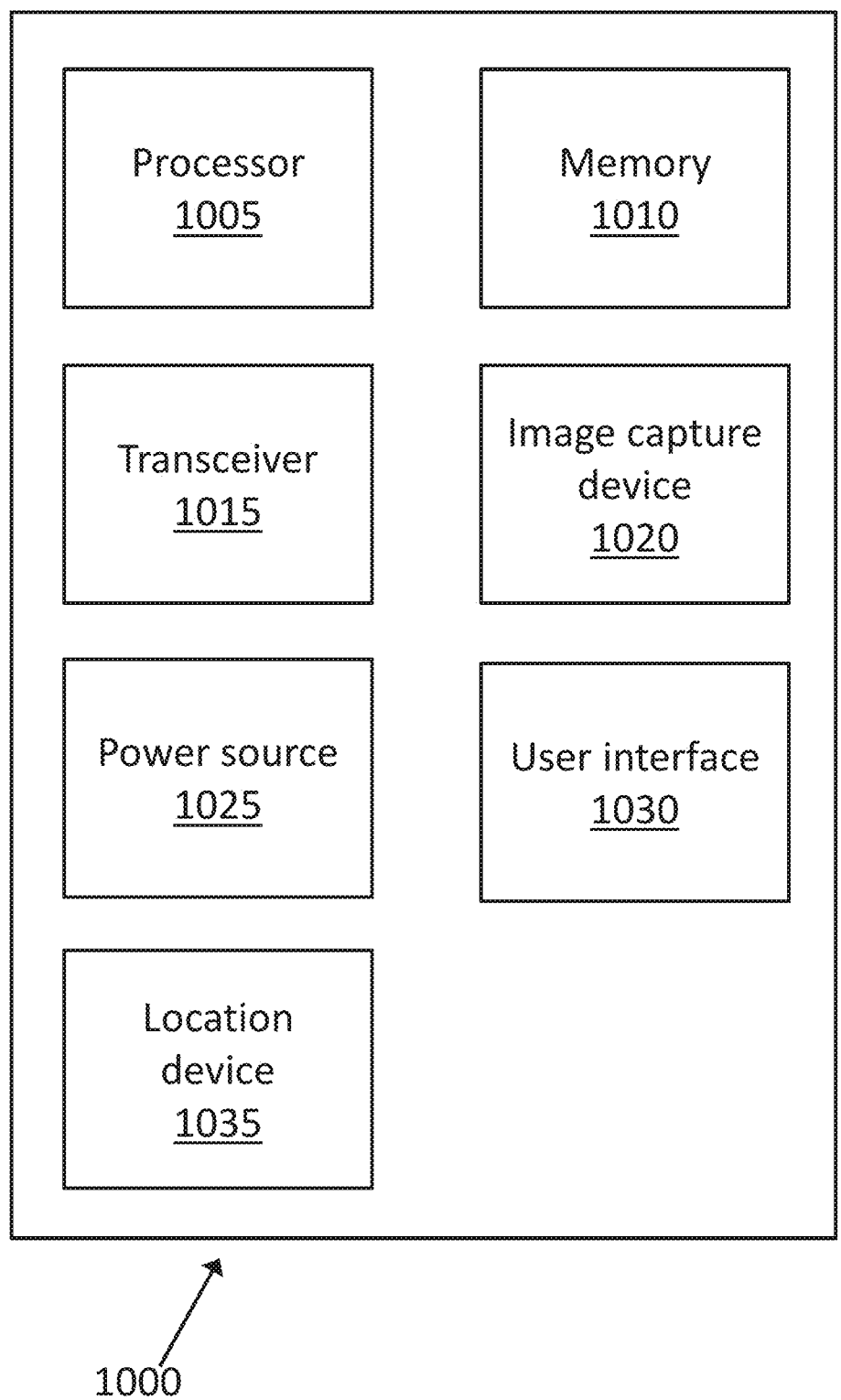
FIG. 10 depicts a block diagram of a machine vision device in accordance with an illustrative embodiment.

FIG. 10 is a block diagram of a machine vision device 1000 in accordance with an illustrative embodiment. In alternative embodiments, additional, fewer, or different elements can be used. Machine vision device 1000 can include a processor 1005, a memory 1010, a transceiver 1015, image capture device 1020, power source 1025, a user interface 1030, and a location device 1035.

In some embodiments, machine vision device 1000 can include processor 1005. Processor 1005 can be configured to carry out and/or cause to be carried out one or more operations described herein. Processor 1005 can execute instructions as known to those skilled in the art. The instructions may be carried out by a special purpose computer, logic circuits, or hardware circuits. Thus, processor 1005 may be implemented in hardware, firmware, software, or any combination of these methods. The term "execution" is the process of running an application or the carrying out of the operation called for by an instruction. The instructions may be written using one or more programming language, scripting language, assembly language, etc. Processor 1005 executes an instruction, meaning that it performs the operations called for by that instruction. Processor 1005 operably couples with memory 1010, transceiver 1015, image capture device 1030, power source 1025, user interface 1030, etc. to receive, to send, and to process information and to control the operations of the machine vision device 1000. Processor 1005 may retrieve a set of instructions from a permanent memory device such as a read-only memory (ROM) device and copy the instructions in an executable form to a temporary memory device that is generally some form of random access memory (RAM). Machine vision device 1000 may include a plurality of processors that use the same or a different processing technology. In an illustrative embodiment, the instructions may be stored in memory 1010.

In some embodiments, machine vision device 1000 can include memory 1010. Memory 1010 can be an electronic holding place or storage for information so that the information can be accessed by processor 1005 as known to those skilled in the art. Memory 1010 can include, but is not limited to, any type of random access memory (RAM), any type of read-only memory (ROM), any type of flash memory, etc. such as magnetic storage devices (e.g., hard disk, floppy disk, magnetic strips, etc.), optical disks (e.g., compact disk (CD), digital versatile disk (DVD), etc.), smart cards, flash memory devices, etc. Machine vision device 1000 may have one or more computer-readable media that use the same or a different memory media technology. Machine vision device 1000 may have one or more drives that support the loading of a memory medium such as a CD, a DVD, a flash memory card, etc. In some embodiments, memory 1010 can be used to store video. Accordingly, in some embodiments, memory 1010 can be used instead of image capture device 1020 to provide video to machine vision device 1000.

In some embodiments, machine vision device 1000 can include a transceiver 1015. Transceiver 1015 can be configured to receive and/or transmit information. In some embodiments, transceiver 1015 can communicate information via a wired connection, such as an Ethernet connection, one or more twisted pair wires, coaxial cables, fiber optic cables, etc. In some embodiments, transceiver 1015 can communicate information via a wireless connection using microwaves, infrared waves, radio waves, spread spectrum technologies, satellites, etc. Transceiver 1015 can be configured to communicate with another device using cellular networks, local area networks, wide are networks, the Internet, etc. In some embodiments, one or more of the elements of machine vision device 1000 communicate via wired or wireless communications.

In some embodiments, machine vision device 1000 can include an image capture device 1020. In other embodiments, image capture device 1020 can be an independent device and not integrated into machine vision device 1000. Image capture device 1020 can be configured to capture images of the real world. In some embodiments, image capture device 1020 can capture two-dimensional images. In other embodiments, image capture device 1020 can capture three-dimensional images. Image capture device 1020 can be a still-image camera, a video camera, etc. Image capture device 1020 can be configured to capture color images, black-and-white images, filtered images (e.g., a sepia filter, a color filter, a blurring filter, etc.), images captured through one or more lenses (e.g., a magnification lens, a wide angle lens, etc.), etc. In some embodiments, image capture device 1020 (and/or processor 1005) can modify one or more image settings or features, such as color, contrast, brightness, white scale, saturation, sharpness, etc.

In some embodiments, machine vision device 1000 can include power source 1025. Power source 1025 can be configured to provide electrical power to one or more elements of machine vision device 1000. In some embodiments, power source 1025 can include an alternating power source, such as available line voltage (e.g., 120 Volts alternating current at 60 Hertz in the United States). Power source 1025 can include one or more transformers, rectifiers, etc. to convert electrical power into power useable by the one or more elements of machine vision device 1000, such as 1.5 Volts, 8 Volts, 12 Volts, 24 Volts, etc. Power source 1025 can include one or more batteries.

In some embodiments, machine vision device 1000 can include user interface 1030. User interface 1030 can be configured to receive and/or provide information from/to a user. User interface 1030 can be any user interface known in the art. User interface 1030 can be an interface for receiving user input and/or machine instructions for entry into machine vision device 1000 as known to those skilled in the art. User interface 1030 may use various input technologies including, but not limited to, a keyboard, a stylus and/or touch screen, a mouse, a track ball, a keypad, a microphone, voice recognition, motion recognition, disk drives, remote controllers, input ports, one or more buttons, dials, joysticks, etc. to allow an external source, such as a user, to enter information into machine vision device 1000. User interface 1030 can be used to navigate menus, adjust options, adjust settings, adjust display, etc.

User interface 1030 can be configured to provide an interface for presenting information from machine vision device 1000 to external systems, users, or memory. For example, user interface 1030 can include an interface for a display, a printer, a speaker, alarm/indicator lights, a network interface, a disk drive, a computer memory device, etc. User interface 1030 can include a color display, a cathode-ray tube (CRT), a liquid crystal display (LCD), a plasma display, an organic light-emitting diode (OLED) display, etc.

In some embodiments, location device 1035 can be used to identify a location, for example, a location of the machine vision device 1000. In some embodiments, location device 1035 can include a global positioning service (GPS) device, a gyroscope, etc. For example, machine vision device 1000 can include a locomotive machine (e.g., a robot, an automobile, etc.) and receive instructions to reach a destination. The machine vision device 1000 can use the location device 1035 to identify the destination and/or a location that that the machine vision device 1000 is currently located. The machine vision device 1000 can use the location device 1035 to navigate to the destination.

As discussed above, machine vision device 1000 can be a stand-alone unit or can be integrated into another system. For example, machine vision device 1000 can be used in conjunction with a locomotive machine to navigate a course.

Although the examples above deal with navigation, facial recognition, and person recognition, it is to be understood that the techniques described herein may be used for a variety of applications including object recognition, emotion/expression recognition, trend recognition in economic/geological/weather, etc. data, disease detection (e.g., using medical images such as MRI images, CT scan images, pathology slides, etc.) and other recognition/detection tasks performed well by animals or humans.

The techniques used herein may be used to process any type of image data. For example, the image data may be generated in response to visible light, but may also be generated by other types of electromagnetic radiation such as infrared, ultraviolet or other wavelengths across the electromagnetic spectrum. In some embodiments, the image data may be artificial or virtual image data (e.g., generated based on a model of a virtual environment). In some embodiments, the artificial image data may be related to the visualization of any kind of suitable data, including for example, medical imaging data (magnetic resonance imaging data, computer aided tomography data), seismic imaging data, LIDAR data, financial data etc.

In various embodiments, the image data may be a single image or a plurality of images; additionally, the images may be static or may vary in a spatiotemporal fashion. Simple shapes such as diagrams or comparatively complex stimuli such as natural scenes may be used. Additionally, the images may be grayscale or in color or combinations of grey and color.

Various implementations of the embodiments discussed above involve a method that includes receiving raw image data corresponding to a series of raw images, processing the raw image data with an encoder to generate encoded data, where the encoder is characterized by an input/output transformation that substantially mimics the input/output transformation of one or more retinal cells of a vertebrate retina, and processing the encoded data to generate dimension reduced encoded data by applying a dimension reduction algorithm configured to compress amount of information contained in the encoded data. The encoded data may include a series of retinal images. The step of processing the encoded data may include processing the series of retinal images to generate feature signature data based on the retinal images. The feature signature data may include information related to a plurality of retinal image regions. The feature signature data may include motion data corresponding to each of the plurality of retinal image regions. The motion data may include speed data corresponding to each of the plurality of retinal image regions. The feature signature data may include optical flow data corresponding to each of the plurality of retinal image regions. The step of processing the encoded data may include applying a trained algorithm to the encoded data. The trained algorithm may include a convolutional neural network (CNN).

The trained algorithm may have been trained on a training data set of encoded training data, and the encoded training data may have been encoded using a training encoder that is characterized by an input/output transformation that substantially mimics the input/output transformation of one or more retinal cells of a vertebrate retina. The training set of encoded training data may include encoded images of a virtual environment, and the raw image data may include raw images of a real environment. The training set of encoded training data may include images acquired under a first set of conditions and the raw image data may include raw images acquired under a second set of conditions different from the first. The first set of conditions and the second set of conditions may include lighting conditions.

The method may further include applying a machine vision algorithm to dimension reduced encoded data. The machine vision algorithm may include at least one select from the list consisting of: an object recognition algorithm, an image classification algorithm, a facial recognition algorithm, an optical character recognition algorithm, a content-based image retrieval algorithm, a pose estimation algorithm, a motion analysis algorithm, an egomotion determination algorithm, a movement tracking algorithm, an optical flow determination algorithm, a scene reconstruction algorithm, a 3D volume recognition algorithm, and a navigation algorithm.

The machine vision algorithm exhibits better performance when applied to the to the dimension reduced encoded data than when applied to a corresponding set of raw images that have not been processed using the encoder or the dimension reduction algorithm. The machine vision algorithm exhibits better performance when applied to the to the dimension reduced encoded data than when applied to a corresponding set of processed raw images that have been processed using the dimension reduction algorithm alone. The machine vision algorithm exhibits better performance when applied to the dimension reduced encoded data than when applied to a corresponding set of encoded images that have not been processed using the dimension reduction algorithm. The machine vision algorithm includes an algorithm for the detection or identification of a person within a series of images, and the machine vision algorithm exhibits better detection or identification accuracy when applied to dimension reduced encoded data based on images including people than when applied to a corresponding set of data that have not been processed using the encoder or the dimension reduction algorithm.

In an implementation of the methods described above, the amount of information contained in the encoded data may be compressed by a factor of at least about 2 relative to the corresponding raw image data, and the dimension reduced encoded data may be compressed by a factor of at least about 2 relative to the corresponding encoded data. The amount of information contained in the encoded data may be compressed by a factor of at least about 5 relative to the corresponding raw image data, and the dimension reduced encoded data may be compressed by a factor of at least about 5 relative to the corresponding encoded data. The amount of information contained in the encoded data may be compressed by a factor of at least about 10 relative to the corresponding raw image data, and the dimension reduced encoded data may be compressed by a factor of at least about 10 relative to the corresponding encoded data.

In an implementation of the methods described above, the vertebrate may include at least one selected from the list consisting of: a mouse, and a monkey. The retinal cells may include ganglion cells. The retinal cells may include one or more classes of cells, and two of the classes of cells may include ON cells and OFF cells. The encoder may be characterized by an input/output transformation that substantially mimics the input/output transformation of one or more retinal cells of a vertebrate retina over a range of input that includes natural scene images including spatio-temporally varying images.

In another implementation, an apparatus includes at least one memory storage device configured to store raw image data; and at least one processor operatively coupled with the memory and programmed to execute the method of any of the preceding paragraphs. The apparatus may further include at least one robotic device operatively coupled to the at least one processor, and the robotic device may include at least one image sensor configured to generate the raw image data. Another implementation includes a non-transitory computer-readable medium having computer-executable instructions for implementing the steps of any of the methods described above.

As used herein the term "light" and related terms (e.g. "optical", "visual") are to be understood to include electromagnetic radiation both within and outside of the visible spectrum, including, for example, ultraviolet and infrared radiation.

While various inventive embodiments have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method comprising:
   processing, by a processing device, image data to generate encoded data; and
   generating, by the processing device, dimension reduced data from the encoded data, wherein generating the dimension reduced data comprises generating feature signature data for a plurality regions in the encoded data, and wherein the feature signature data comprises components having values associated with respective regions of a plurality of regions of the encoded data; and
   wherein generating dimension reduced data comprises applying a dimension reduction algorithm to the encoded data, wherein the dimension reduction algorithm selects a subset of features of the encoded data for a specific machine vision task and ignores other features of the encoded data for the specific machine vision task.

2. The method of claim 1, wherein the feature signature data comprises a vector having components that comprise values of a subset of features associated with the respective regions of the plurality of regions.

3. The method of claim 1, wherein processing the image data to generate encoded data comprises dimensionally reducing the image data, and wherein generating the dimension reduced data from the encoded data comprises an additional dimension reduction operation comprising additionally compressing the encoded data that is already dimensionally reduced relative to the image data.

4. The method of claim 1, further comprising receiving the image data at the processing device from a camera.

5. The method of claim 1, wherein the feature signature data comprises motion data corresponding to each of the plurality of regions of the encoded data.

6. The method of claim 5, wherein the motion data comprises speed data corresponding to each of the plurality of regions of the encoded data.

7. The method of claim 1, wherein the feature signature data comprises optical flow data corresponding to each of the plurality of regions of the encoded data.

8. The method of claim 1, further comprising generating, by the processing device, one or more encoded retinal images from the encoded data, wherein generating the dimension reduced data from the encoded data comprises generating the dimension reduced data from the one or more encoded retinal images, and wherein generating the one or more encoded retinal images comprises applying a trained algorithm to the encoded data.

9. The method of claim 8, wherein the trained algorithm comprises a convolutional neural network.

10. The method of claim 8, wherein the trained algorithm has been trained on a training data set of encoded training data, and wherein the encoded training data has been encoded using a training encoder that is characterized by an input/output transformation that substantially mimics the input/output transformation of one or more retinal cells of a vertebrate retina.

11. The method of claim 10, wherein the training set of encoded training data comprises encoded images of a virtual environment, and the image data comprise raw images of a real environment.

12. The method of claim 1, further comprising applying a machine vision algorithm to the dimension reduced data.

13. The method of claim 12, generating the dimension reduced data is performed after the processing the image data to generate encoded data and before the applying the machine vision algorithm to the dimension reduced data.

14. The method of claim 1, wherein processing the image data comprises converting the image data to one or more firing rates, wherein the encoded data comprises a matrix of firing rates and one or more encoded retinal images, and wherein the one or more encoded retinal images comprises a firing rate retinal image.

15. The method of claim 14, wherein the firing rate retinal image comprises a plurality of pixels, and wherein each pixel of the plurality of pixels has a respective intensity that corresponds to a firing rate value of a corresponding element in the matrix of firing rates.

16. The method of claim 14, further comprising generating the one or more encoded retinal images by, at least in part, converting a pixel intensity to a firing rate.

17. An apparatus comprising:
at least one memory configured to store image data; and
at least one processor operatively coupled with the memory and programmed to:
process the image data to generate encoded data; and
generate dimension reduced data from the encoded data, wherein generating the dimension reduced data comprises generating feature signature data for a plurality regions in the encoded data, and wherein the feature signature data comprises components having values associated with respective regions of a plurality of regions of the encoded data; and
wherein, to generate the dimension reduced data, the at least one processor is further configured to apply a dimension reduction algorithm to the encoded data, and wherein the dimension reduction algorithm selects a subset of features of the encoded data for a specific machine vision task and ignores other features of the encoded data for the specific machine vision task.

18. The apparatus of claim 17, further comprising:
a robotic device operatively coupled to the at least one processor, wherein the robotic device comprises at least one image sensor configured to generate the image data; and
a machine vision module configured to control the robotic device in accordance with the dimension reduced data.

19. A non-transitory computer-readable medium having computer-executable instructions that, upon execution by a computing device, cause the computing device to perform operations comprising:
processing image data to generate encoded data; and
generating dimension reduced data from the encoded data, wherein generating the dimension reduced data comprises generating feature signature data for a plurality regions in the encoded data, and wherein the feature signature data comprises components having values associated with respective regions of a plurality of regions of the encoded data; and
wherein generating dimension reduced data comprises applying a dimension reduction algorithm to the encoded data, wherein the dimension reduction algorithm selects a subset of features of the encoded data for a specific machine vision task and ignores other features of the encoded data for the specific machine vision task.

* * * * *